United States Patent
Ito et al.

(10) Patent No.: US 6,566,535 B1
(45) Date of Patent: May 20, 2003

(54) PROCESSES FOR THE PREPARATION OF 2, 3-DIHYDROTHIEPINE DERIVATIVES

(75) Inventors: Tatsuya Ito, Kashiba (JP); Tomomi Ikemoto, Takarazuka (JP); Kiminori Tomimatsu, Minoo (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/019,987

(22) PCT Filed: May 18, 2000

(86) PCT No.: PCT/JP00/03182

§ 371 (c)(1),
(2), (4) Date: Nov. 7, 2001

(87) PCT Pub. No.: WO00/69845

PCT Pub. Date: Nov. 23, 2000

(30) Foreign Application Priority Data

May 18, 1999  (JP) ............................................ 11-137387

(51) Int. Cl.⁷ ........................ C07D 337/12; C07L 45/00
(52) U.S. Cl. ......................................... 549/12; 568/426
(58) Field of Search ............................. 549/12; 568/426

(56) References Cited

U.S. PATENT DOCUMENTS

| | | | |
|---|---|---|---|
| 4,436,749 A | | 3/1984 | Hatinguais .................. 548/355 |
| 5,716,944 A | | 2/1998 | Sohda ......................... 514/119 |
| 5,952,512 A | * | 9/1999 | Maeda et al. .................. 549/12 |
| 5,994,391 A | * | 11/1999 | Lee et al. ................... 514/431 |
| 6,111,115 A | * | 8/2000 | Yamamoto et al. ............ 549/12 |

FOREIGN PATENT DOCUMENTS

| | | |
|---|---|---|
| WO | WO 96/08484 | 3/1996 |
| WO | WO 97/3382 | 9/1997 |
| WO | WO 98/55475 | 12/1998 |
| WO | WO 99/32100 | 7/1999 |
| WO | WO 99/32468 | 7/1999 |
| WO | WO 00/10965 | 3/2000 |
| WO | WO 00/37455 | 6/2000 |
| WO | WO 00/68203 | 11/2000 |

OTHER PUBLICATIONS

Buckle et al. "Synthesis of Aryloxy Analogues of Arachidonic Acid via Wittig and Palladium–catalysed Cross–coupling reactions" J. Chem Research(S) (1987), 394–395; J. Chem Research(M) (1987), 3144–3177.

Baba et al. "A small molecule, non–peptide CCR5 antagonist with high potent and selective anti–HIV-1 activity" PNAS(USA) 96:5698–5703 (1999).

* cited by examiner

Primary Examiner—Deborah C. Lambkin
(74) Attorney, Agent, or Firm—Mark Chao; Elaine M. Ramesh

(57) ABSTRACT

A process for preparing a compound represented by the following formula:

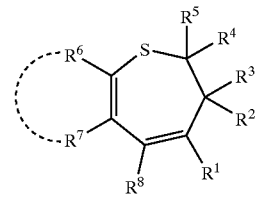

wherein each symbol is as defined below, or a salt thereof, characterized by subjecting a compound represented by the following formula:

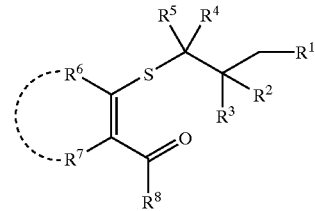

wherein $R^1$ is an electron-attracting group; $R^2$, $R^3$, $R^4$, $R^5$, $R^6$ and $R^7$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, provided that $R^6$ and $R^7$ may be united to form a ring; and $R^8$ is a hydrogen atom or an optionally substituted hydrocarbon group, or a salt thereof, to a ring-closing reaction.

36 Claims, No Drawings

PROCESSES FOR THE PREPARATION OF 2, 3-DIHYDROTHIEPINE DERIVATIVES

This application is a 371 of PCT/JP00/03182 May 18, 2000.

TECHNICAL FIELD

The present invention relates to processes for the preparation of 2,3-dihydrothiepine derivatives.

BACKGROUND ART

Heretofore, a process for synthesizing a 2,3-dihydrobenzothiepine derivative by subjecting phenylthiobutyric acid to an intramolecular cyclodehydration, introducing a C1 unit into the α-position of the obtained ketone body, and conducting reduction and dehydration is disclosed in patent applications such as PCT/JP98/05708 (WO99/32100) and Japanese Patent Application No. 10-363404 (PCT/JP99/07148). Moreover, as a cyclization reaction of the Dieckmann type, a process proposed by Nagamatsu et al., (J. Heterocyclic Chem., 28, 513 (1991)), a process disclosed in WO098/55475, etc. are known. However, these processes use raw material difficult to get, reagents having a disposal problem or reagents not suitable for large-scale synthesis. In addition, the processes have long steps and require complicated operations.

Because of the above-mentioned present conditions, there is a demand for a process for producing a 2,3-dihydrothiepine derivative, the process being inexpensive, simple and more suitable for large-scale synthesis.

DISCLOSURE OF INVENTION

The inventors of the present invention made a variety of studies, and as a result, they have found a process for preparing a 2,3-dihydrothiepine derivative by causing a sulfide having a propyl group as a substituent, the propyl group having an α,β unsaturated carbonyl group and an electron-attracting group at its end, to react with a base in a solvent. Furthermore, they found a process for preparing a 2,3-dihydrothiepine derivative by causing an orthohalogenobenzaldehyde to react with a propanethiol having an electron-attracting group at its 4-position. As a result of further studies based on these findings, they have accomplished the present invention.

Namely, the present invention relates to:

(1) a process for preparing a compound represented by the following formula:

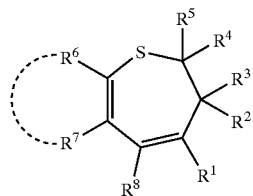

wherein each symbol is as defined below, or a salt thereof, characterized by subjecting a compound represented by the following formula:

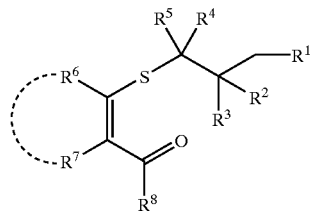

wherein $R^1$ is an electron-attracting group; $R^2$, $R^3$, $R^4$, $R^5$ $R^6$ and $R^7$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, provided that $R^6$ and $R^7$ may be united to form a ring; and $R^8$ is a hydrogen atom or an optionally substituted hydrocarbon group, or a salt thereof, to a ring-closing reaction;

(2) the preparation process according to the above-mentioned (1) wherein $R^1$ is an esterified carboxyl group;

(3) the preparation process according to the above-mentioned (1) wherein $R^8$ is a hydrogen atom;

(4) the preparation process according to the above-mentioned (1) wherein $R^2$, $R^3$, $R^4$ and $R^5$ are each a hydrogen atom;

(5) the preparation process according to the above-mentioned (1) wherein the reaction is conducted in the presence of a base;

(6) the preparation process according to the above-mentioned (5) wherein the base is an alcoholate;

(7) the preparation process according to the above-mentioned (1) wherein the reaction is conducted in a solvent containing a carbonic acid diester;

(8) a process for preparing a compound represented by the following formula:

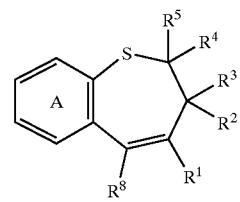

wherein each symbol is as defined below, or a salt thereof, characterized by subjecting a compound represented by the following formula:

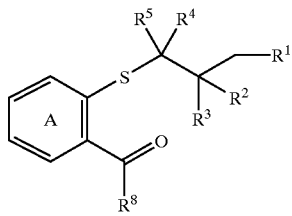

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; ring A is an optionally substituted benzene ring; and $R^8$ is a hydrogen atom or an optionally substituted hydrocarbon group, or a salt thereof, to a ring-closing reaction;

(9) the preparation process according to the above-mentioned (8) wherein $R^1$ is an esterified carboxyl group;

(10) the preparation process according to the above-mentioned (8) wherein $R^8$ is a hydrogen atom;

(11) the preparation process according to the above-mentioned (8) wherein $R^2$, $R^3$, $R^4$ and $R^5$ are each a hydrogen atom;

(12) the preparation process according to the above-mentioned (8) wherein the reaction is conducted in the presence of a base;

(13) the preparation process according to the above-mentioned (12) wherein the base is an alcoholate;

(14) the preparation process according to the above-mentioned (8) wherein the reaction is conducted in a solvent containing a carbonic acid diester;

(15) a process for preparing a compound represented by the following formula:

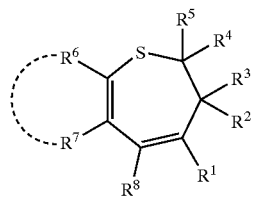

wherein each symbol is as defined below, or a salt thereof, characterized by causing a compound represented by the following formula:

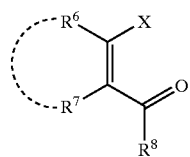

wherein X is a leaving group; and $R^6$ and $R^7$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, provided that $R^6$ and $R^7$ may be united to form a ring; and $R^8$ is a hydrogen atom or an optionally substituted hydrocarbon group, or a salt thereof, to react with a compound represented by the following formula:

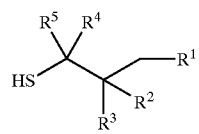

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, or a salt;

(16) the preparation process according to the above-mentioned (15) wherein X is a halogen atom;

(17) the preparation process according to the above-mentioned (15) wherein X is a fluorine atom;

(18) the preparation process according to the above-mentioned (15) wherein $R^1$ is an esterified carboxyl group;

(19) the preparation process according to the above-mentioned (15) wherein $R^8$ is a hydrogen atom;

(20) the preparation process according to the above-mentioned (15) wherein $R^2$, $R^3$, $R^4$ and $R^5$ are each a hydrogen atom;

(21) A process for preparing a compound represented by the following formula:

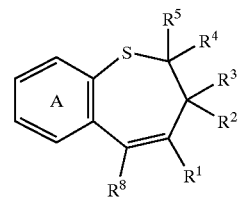

wherein each symbol is as defined below, or a salt thereof, characterized by causing a compound represented by the following formula:

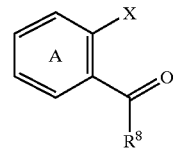

wherein X is a leaving group; $R^8$ is a hydrogen atom or an optionally substituted hydrocarbon group; and ring A is an optionally substituted benzene ring, or a salt thereof, to react with a compound represented by the following formula:

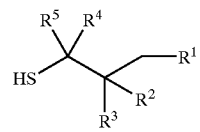

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, or a salt thereof;

(22) the preparation process according to the above-mentioned (21) wherein X is a halogen atom;

(23) the preparation process according to the above-mentioned (21) wherein X is a fluorine atom;

(24) the preparation process according to the above-mentioned (21) wherein $R^1$ is an esterified carboxyl group;

(25) the preparation process according to the above-mentioned (21) wherein $R^8$ is a hydrogen atom;

(26) the preparation process according to the above-mentioned (21) wherein $R^2$, $R^3$, $R^4$ and $R^5$ are each a hydrogen atom;

(27) a process for preparing a compound represented by the following formula:

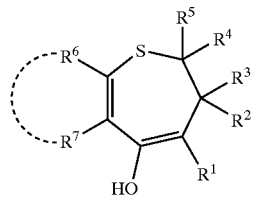

wherein each symbol is as defined below, or a salt thereof, characterized by subjecting a compound represented by the following formula:

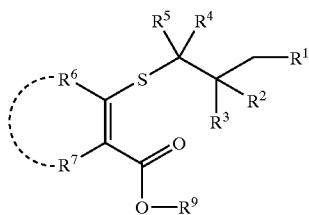

wherein $R^1$ is an electron-attracting group; $R^2$, $R^3$, $R^4$, $R^5$, $R^6$ and $R^7$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; and $R^9$ is an optionally substituted hydrocarbon group; provided that $R^6$ and $R^7$ may be united to form a ring, or a salt thereof, to a ring-closing reaction in the presence of an alcoholate in a solvent containing a carbonic acid diester;

(28) the preparation process according to the above-mentioned (27) wherein $R^1$ is an esterified carboxyl group;

(29) the preparation process according to the above-mentioned (27) wherein each of $R^2$, $R^3$, $R^4$ and $R^5$ is hydrogen;

(30) a process for preparing a compound represented by the following formula:

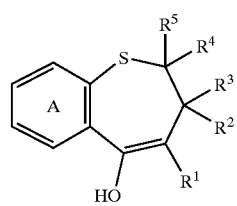

wherein each symbol is as defined below, or a salt thereof, characterized by subjecting a compound represented by the following formula:

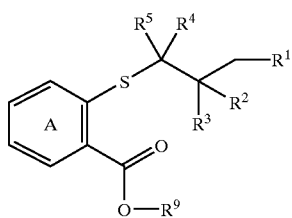

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; $R^9$ is an optionally substituted hydrocarbon group; and ring A is an optionally substituted benzene ring, or a salt thereof, to a ring-closing reaction in the presence of an alcoholate in a solvent containing a carbonic acid diester;

(31) the preparation process according to the above-mentioned (30) wherein $R^1$ is an esterified carboxyl group;

(32) the preparation process according to the above-mentioned (30) wherein each of $R^2$, $R^3$, $R^4$ and $R^5$ is hydrogen;

(33) a compound represented by the following general formula:

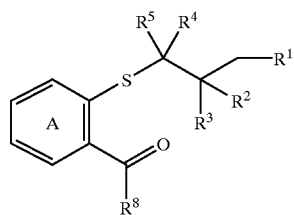

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; ring A is an optionally substituted benzene ring; and $R^8$ is a hydrogen atom or an optionally substituted hydrocarbon group, or a salt thereof;

(34) the preparation process according to the above-mentioned (33) wherein $R^1$ is an optionally esterified carboxyl group;

(35) the preparation process according to the above-mentioned (33) wherein $R^8$ is a hydrogen atom;

(36) the preparation process according to the above-mentioned (33) wherein $R^2$, $R^3$, $R^4$ and $R^5$ are each a hydrogen atom;

(37) a process for preparing a compound represented by the following formula:

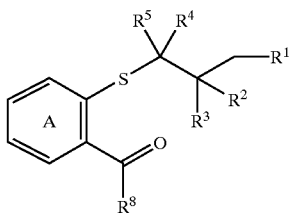

wherein each symbol is as defined below, or a salt thereof, characterized by causing a compound represented by the following formula:

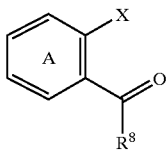

wherein X is a leaving group; $R^8$ is a hydrogen atom or an optionally substituted hydrocarbon group; and ring A is an optionally substituted benzene ring, or a salt thereof, to react with a compound represented by the following formula:

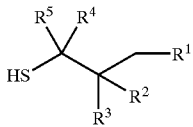

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, or a salt;

(38) the preparation process according to the above-mentioned (37) wherein $R^1$ is an esterified carboxyl group;

(39) the preparation process according to the above-mentioned (37) wherein $R^8$ is a hydrogen atom;

(40) the preparation process according to the above-mentioned (37) wherein $R^2$, $R^3$, $R^4$ and $R^5$ are each a hydrogen atom;

(41) the preparation process according to the above-mentioned (37) wherein X is a halogen atom; and

(42) the preparation process according to the above-mentioned (37) wherein X is a fluorine atom.

The "electron-attracting group" used in this specification is exemplified by (i) optionally esterified or amidated carboxyl groups; (ii) groups represented by the formula: —(CO)$R^9$, wherein $R^9$ is an optionally substituted hydrocarbon group; (iii) a nitrile group; (iv) a nitro group; (v) groups represented by the formula: —(SO$_m$)$R^{10}$, wherein m is 1 or 2 and $R^{10}$ is an optionally substituted hydrocarbon group; (vi) groups represented by the formula: —P$R^{11}R^{12}$, wherein $R^{11}$ and $R^{12}$ are each an optionally substituted hydrocarbon group; (vii) groups represented by the formula: —(PO)(O$R^{13}$)(O$R^{14}$), wherein $R^{13}$ and $R^{14}$ are each hydrogen or an optionally substituted hydrocarbon group; (viii) optionally substituted aryl groups; (ix) optionally substituted alkenyl groups; (x) halogen atoms (for example, fluorine, chlorine, bromine and iodine); and (xi) a nitroso group, preferably by optionally esterified or amidated carboxyl groups, groups represented by the formula: —(CO)$R^9$, a nitrile group, a nitro group, groups represented by the formula: —(SO$_m$)$R^{10}$, groups represented by the formula: —P$R^{11}R^{12}$ and groups represented by the formula: —(PO)(O$R^{13}$)(O$R^{14}$), and more preferably by esterified carbonyl groups (for example, carbonyl groups esterified with $C_{1-4}$ alkyl such as methoxycarbonyl, ethoxycarbonyl and t-butoxycarbonyl.)

The "esterified carboxyl groups" in the above-mentioned (i) "optionally esterified of amidated carboxyl groups" are exemplified by groups represented by the formula: —(CO)O$R^{15}$, wherein $R^{15}$ is hydrogen or an optionally substituted hydrocarbon group and the "amidated carboxyl groups" are exemplified by groups represented by the formula: —(CO)N$R^{16}R^{17}$, wherein $R^{16}$ and $R^{17}$ are each hydrogen or an optionally substituted hydrocarbon group and also may be united to form a 5- to 7-membered (preferably, a 5- to 6-membered) cyclic amino together with the nitrogen atom adjoining $R^{16}$ and $R^{17}$, such as tetrahydropyrrole, piperazine, piperidine, morpholine, thiomorpholine, pyrrole and imidazole.

In the above-recited formula (vi) or (vii), $R^{11}$ and $R^{12}$, or $R^{13}$ and $R^{14}$ may be united to form, for example, a lower ($C_{2-6}$) alkylene (for example, dimethylene, trimethylene and tetramethylene), a lower ($C_{2-6}$) alkenylene (for example, —CH$_2$—CH=CH—, —CH$_2$—CH$_2$—CH=CH— and —CH$_2$—CH=CH—CH$_2$—), and a lower ($C_{4-6}$) alkadienylene (for example, —CH=CH—CH=CH—), preferably a lower ($C_{1-6}$) alkylene, more preferably a lower ($C_{4-6}$) alkylene. These divalent groups may have a substituent, whose examples include a hydroxyl group, halogens, $C_{1-4}$ alkyls, $C_{1-4}$ alkoxys.

The "aryl groups" in the above-mentioned (viii) optionally substituted aryl groups are exemplified by $C_{6-14}$ aryls such as phenyl and naphthyl, preferably $C_{6-10}$ aryls, and more preferably phenyl. The aryl groups may have from one to three substituents such as those the below-mentioned "optionally substituted hydrocarbon groups" may have.

The "alkenyl groups" in the above-mentioned (ix) optionally substituted alkenyl groups are exemplified by alkenyls having from two to ten carbon atoms such as vinyl, allyl, crotyl, 2-pentenyl and 3-hexenyl, preferably lower ($C_{2-6}$) alkenyls, and more preferably vinyl. The alkenyl groups may have from one to three substituents such as those the below-mentioned "optionally substituted hydrocarbon groups " may have.

The "hydrocarbon groups" in the "optionally substituted hydrocarbon groups" used in this specification are exemplified by (1) alkyls (for example, $C_{1-10}$ alkyls such as methyl, ethyl, propyl, isopropyl, butyl, isobutyl, sec-butyl, tert-butyl, pentyl, isopentyl, neopentyl, hexyl, heptyl, octyl, nonyl, and decyl, and preferably lower ($C_{1-6}$) alkyls);

(2) cycloalkyls (for example, $C_{3-7}$ cycloalkyls such as cyclopropyl, cyclobutyl, cyclopentyl, cyclohexyl and cycloheptyl);

(3) alkenyls (for example, alkenyls having from two to ten carbon atoms such as vinyl, allyl, crotyl, 2-pentenyl and 3-hexenyl);

(4) cycloalkenyls (for example, cycloalkenyls having from three to seven carbon atoms such as 2-cyclopentenyl, 2-cyclohexenyl, 2-cyclopentenylmethyl and 2-cyclohexenylmethyl);

(5) alkynyls (for example, alkynyl having from two to ten carbon atoms such as ethynyl, 1-propynyl, 2-propynyl, 1-butynyl, 2-pentynyl and 3-hexynyl, and preferably lower ($C_{2-6}$) alkynyls)

(6) aryls (for example, $C_{6-14}$ aryls such as phenyl and naphthyl, preferably $C_{6-10}$ aryls, and more preferably phenyl);

(7) aralkyls (for example, phenyl-$C_{1-4}$ alkyls (example, benzyl and phenethyl)). Particularly, alkyls are preferable and $C_{1-4}$ alkyls such as methyl and ethyl are more preferable. Especially, methyl is preferably used.

The hydrocarbon groups may have a substituent, examples of which include halogens (for example, fluorine, chlorine, bromine and iodine), nitro, cyano, a hydroxyl group, optionally substituted thiol groups (for example, thiol and $C_{1-4}$ alkylthios), optionally substituted amino groups (for example, amino, mono-$C_{1-4}$ alkylamino, di-$C_{1-4}$ alkylamino, and 5- to 6-membered cyclic aminos such as tetrahydropyrrole, piperazine, piperidine, morpholine, thio morpholine, pyrrole and imidazole), optionally esterified or amidated carboxyl groups (for example, carboxyl, $C_{1-4}$ alkoxycarbonyl, carbamoyl, mono-$C_{1-4}$ alkylcarbamoyls and di-$C_{1-4}$ alkylcarbamoyls), $C_{1-4}$ alkyls which may be substituted with a halogen atom or a $C_{1-4}$ alkoxy (for example, trifluoromethyl, methyl and ethyl), $C_{1-4}$ alkoxys which may be substituted with a halogen atom or a $C_{1-4}$ alkoxy (for example, methoxy, ethoxy, trifluoromethoxy and trifluoroethoxy), formyl, $C_{2-4}$ alkanoyls (for example, acetyl and propionyl), $C_{1-4}$ alkylsulfonyls (for example, methanesulfonyl and ethanesulfonyl), and $C_{1-4}$ alkylsulfinyls (for example, methanesulfinyl and ethanesulfinyl). The number of such substituents is preferably from one to three.

Examples of the "halogen atom" represented by $R^2$, $R^3$, $R^4$ $R^5$, $R^6$ and $R^7$ in the above-recited formulas include fluorine, chlorine, bromine and iodine.

Examples of the "optionally substituted amino groups" represented by $R^2$, $R^3$, $R^4$, $R^5$, $R^6$ and $R^7$ in the above-recited formulas include amino groups that may be substituted with the above-mentioned "optionally substituted hydrocarbon groups." The number of such substituents may be any of one to two. When two substituents are present, the two substituents may be the same or different. The two substituents may be united to form 5- to 7-membered (preferably 5- to 6-membered) cyclic amino (for example, tetrahydropyrrole, piperazine, piperidine, morpholine, thiomorpholine, pyrrole and imidazole) together with a nitrogen atom adjoining the two substituents.

Examples of the "optionally substituted hydroxyl groups" represented by $R^2$, $R^3$, $R^4$, $R^5$, $R^6$ and $R^7$ in the above-recited formulas include hydroxyl groups that may be substituted with the above-mentioned "optionally substituted hydrocarbon groups."

Examples of the "optionally substituted thiol groups" represented by $R^2$, $R^3$, $R^4$, $R^5$, $R^6$ and $R^7$ in the above-recited formulas include thiol groups that may be substituted with the above-mentioned "optionally substituted hydrocarbon groups."

The "heterocyclic group" in the "optionally substituted heterocyclic group" used in this specification is exemplified by 5- to 7-membered aromatic heterocyclic rings containing from one to three kinds (preferably, from one to two kinds) of at least one (preferably, from one to four, more preferably from one to two) hetero atoms selected form an oxygen atom, a sulfur atom, a nitrogen atom and the like, and saturated or unsaturated non-aromatic heterocyclic rings (aliphatic heterocyclic rings).

Examples of the "aromatic heterocyclic rings" include 5- to 6-membered monocyclic heterocyclic rings (for example, furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine and triazine). Examples of the "non-aromatic heterocyclic rings" include 5- to 7-membered (preferably, 5- to 6-membered) saturated or unsaturated (preferably, saturated) non-aromatic heterocyclic rings (aliphatic heterocyclic rings) and the like, or 5- to 6-membered non-aromatic heterocyclic rings resulting from a part or all of the double bonds of the above-mentioned aromatic monocyclic heterocyclic rings. As such heterocyclic rings, 5- to 6-membered aromatic rings are desirable, and furan, thiophene, pyrrole, pyridine (preferably, 6-membered rings) and the like are more desirable.

The substituents which the heterocyclic rings may have are exemplified by substituents such as those the above-mentioned "optionally substituted hydrocarbon groups." The number of such substituents may be from one to three.

In the above-recited formulas, an esterified carboxyl group is desirable as $R^1$, and a hydrogen atom is desirable as $R^8$. As $R^2$, $R^3$, $R^4$ and $R^5$, a hydrogen atom or optionally substituted hydrocarbon groups are desirable and a hydrogen atom is more desirable. $R^6$ and $R^7$ are preferably united to form an optionally substituted benzene ring.

The substituent which the "optionally substituted benzene ring" used in this specification may have is exemplified by substituents such as those the above-mentioned "optionally substituted hydrocarbon groups" may have; the above-mentioned "optionally substituted aryl groups" which may be combined through a spacer (for example, divalent groups having from one to four atoms constituting a linear portion) (preferably, the above-mentioned "optionally substituted aryl groups" directly combined). Particularly, such substituents are preferably electron-attracting groups. The number of such substituents may be from one to four.

Examples of the spacer include —$(CH_2)_a$— [a is an integer of from 1 to 4 (preferably an integer of from 1 to 2)], —$(CH_2)_b$—$X^a$— [b is an integer of from 0 to 3 (preferably an integer of from 0 to 1) and $X^a$ is an optionally substituted imino group (for example, an imino group which may be substituted with lower ($C_{1-6}$) lower alkyl, lower ($C_{3-7}$) cycloalkyl, formyl, lower ($C_{2-7}$) lower alkanoyl, lower ($C_{1-6}$) lower alkoxy-carbonyl or the like), a carbonyl group, an oxygen atom or a sulfur atom which may be oxidized (for example, —S(O)$_n$— (n is an integer of from 0 to 2)), —CH=CH—, —C≡C—, —CO—NH— and —SO$_2$—NH— (preferably —$(CH_2)_b$—$X_a$—, more preferably —$CH_2$—O—). Such groups may be combined with an "optionally substituted benzene ring" through either of their right and left bonds, but they are preferably combined with an "optionally substituted benzene ring" through their right bonds.

Examples of the ring formed from $R^6$ and $R^7$ united together include 5- to 7-membered (preferably 5- to 6-membered) unsaturated alicyclic hydrocarbons such as $C_{5-7}$ cycloalkenes (for example, 1-cyclopentene, 2-cyclopentene, 3-cyclopentene, 2-cyclohexene and 3-cyclohexene), $C_{5-6}$ cycloalkadienes (for example, 2,4-cyclopentadiene, 2,4-cyclohexadiene and 2,5-cyclohexadiene). The aromatic-hydrocarbon; 6-membered aromatic hydrocarbons such as benzene; 5- to 7-membered aromatic heterocyclic rings containing from one to three kinds (preferably, from one to two kinds) of at least one (preferably, from one to four, more preferably from one to two) hetero atoms selected form an oxygen atom, a sulfur atom, a nitrogen atom and the like, and unsaturated non-aromatic heterocyclic rings (aliphatic heterocyclic rings).

Examples of the "aromatic heterocyclic rings" as a ring which $R^6$ and $R^7$ are united to form include 5- to 6-membered monocyclic heterocyclic rings (for example, furan, thiophene, pyrrole, oxazole, isoxazole, thiazole, isothiazole, imidazole, pyrazole, 1,2,3-oxadiazole, 1,2,3-thiadiazole, 1,2,3-triazole, pyridine, pyridazine, pyrimidine and pyrazine). Examples of the "non-aromatic heterocyclic rings" as a ring which $R^6$ and $R^7$ are united to form include 5- to 6-membered non-aromatic heterocyclic rings resulting from a part of the double bonds of the above-mentioned aromatic monocyclic heterocyclic rings.

As the ring which $R^6$ and $R^7$ are united to form, 5- to 6-membered aromatic rings are desirable, and benzene, furan, thiophene, pyrrole, pyridine (preferably 6-membered rings) and the like are more desirable, and benzene is especially desirable.

The rings which $R^6$ and $R^7$ are united to form may have a substituent, examples of which include substituents such as those the "benzene ring" of the above-mentioned "optionally substituted benzene ring" may have. From one to three, different or the same substituent may substitute at any position where the benzene ring can be substituted.

Examples of the leaving group used in this specification include halogen atoms (for example, fluorine, chlorine, bromine and iodine) and groups represented by the formula —O(SO$_m$)R [in the formula, m is 1 or 2, R is an optionally substituted hydrocarbon group (preferably, optionally halogenated $C_{1-4}$ alkyl, more preferably trifluoromethyl)]. Among these examples, halogen atoms are desirable, and especially, a fluorine atom and a bromine atom are desirable.

When a compound having such a substituent is a basic compound depending upon the type of the substituents mentioned above, it could be converted to a salt using an acid according to conventional methods. Such an acid may be any one that does not affect the reaction. For example, inorganic acids such as hydrochloric acid, hydrobromic acid, phosphoric acid, sulfuric acid, nitric acid and sulfamic acid, organic acids such as formic acid, acetic acid, trifluoroacetic acid, tartaric acid, citric acid, fumaric acid, maleic acid, succinic acid, malic acid, p-toluenesulfonic acid, methanesulfonic acid and benzenesulfonic acid, acidic amino acids such as aspartic acid and glutamic acid, etc. can be mentioned. Moreover, when the compound obtained is a salt, it may be converted to a free base according to conventional methods.

On the other hand, when a compound having such a substituent is an acidic compound depending upon the type of the substituents mentioned above, it could be converted to a salt using a base according to conventional methods. Such a base may be any one that does not affect the reaction. For example, salts with inorganic bases, salts with organic bases and salts with basic amino acids can be mentioned. Suitable examples of the salts with inorganic bases include alkali metal salts such as sodium salts and potassium salts; alkaline earth metal salts such as calcium salts and magnesium salts; aluminum salts and ammonium salts. Suitable examples of the salts with organic bases include salts with trimethylamine, triethylamine, pyridine, picoline, ethanolamine, diethanolamine, triethanolamine, dicyclohexylamine, N,N'-dibenzylethylenediamine. Suitable examples of the salts with basic amino acids include salts with arginine, lysine and ornithine. Moreover, when the compound obtained is a salt, it may be converted to a free acid according to conventional methods.

As the "carbonic acid diester" used in this specification, compounds represented by Z—O(CO)O—Z' wherein Z and Z' independently represent an optionally substituted hydrocarbon group (preferably, an optionally substituted alkyl group) can be mentioned. However, compounds which are liquid at a reaction temperature at which the reaction of the present invention is conducted. Moreover, it is desirable that Z and Z' are the same. As the carbonic acid diesters, carbonic acid di-$C_{1-4}$ alkyl esters such as dimethyl carbonate and diethyl carbonate are preferably used.

The reaction shown in the above-mentioned (1) is conducted under, for example, the conditions described above.

A compound represented by the following formula:

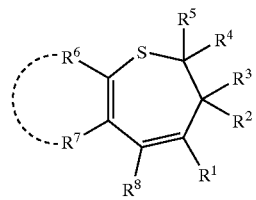

wherein each symbol is as defined above, or a salt thereof is prepared by subjecting a compound represented by the following formula:

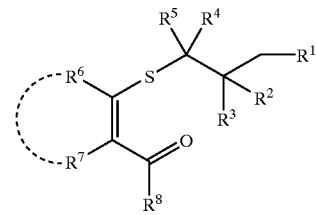

wherein each symbol is as defined above, or a salt thereof, to a ring-closing reaction.

The reaction shown in the above-mentioned (1) is preferably conducted in the presence of a base. Examples of such a base include metal hydrogen compounds (for example, hydrides of alkali metals such as sodium hydride and potassium hydride), metal hydrocarbons (for example, compounds having a chemical bond which combines $C_{1-4}$ alkyl with an alkali metal directly, such as n-butyllithium), alcoholates (for example, compounds which results from substitution of the hydrogen of a hydroxyl group of a $C_{1-4}$ alcohol with an alkali metal, such as NaOMe, NaOEt, t-BuONa, and t-BuOK), hydroxides of alkali metals (for example, NaOH and KOH), basic carbonates (for example, salts of alkali metals such as sodium salts and potassium salts, and alkaline earth metal salts such as calcium salts and magnesium salts), basic hydrogencarbonates (for example, hydrogencarbonates with alkali metal salts such as sodium salts and potassium salts), organic bases (for example, trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane and 1,8-diazabicyclo[5.4.0]-7-undecene). Metal hydrogen compounds (for example, sodium hydride and potassium hydride) and alcoholates (for example, NaOMe, NaOEt, t-BuONa, and t-BuOK) are desirably employed, and especially, alcoholates (for example, NaOMe, NaOEt, t-BuONa, and t-BuOK) are preferably employed.

The amount of the base used in the reaction of the above-mentioned (1) is about 0.1 to 100 equivalents, preferably about 1 to 5 equivalents.

Examples of solvents preferably employed include halogen-containing solvents (for example, methylene chloride, dichloroethane and chloroform), aliphatic hydrocarbons (for example, n-hexane), aromatic hydrocarbons (for example, benzene and toluene), ethers (for example, tetrahydrofuran (THF) and diethyl ether), polar solvents (for example, dimethylformamide (DMF) and dimethyl sulfoxide (DMSO)), carbonic acid diesters (for example, di-$C_{1-4}$ alkyl carbonates such as dimethyl carbonate and diethyl carbonate), formates (for example, $C_{1-4}$ alkyl formate), oxalic acid diesters (for example, di-$C_{1-4}$ alkyl oxalates), alcohols (for example, methanol, ethanol, propanol, isopropanol, n-butanol and 2-methoxyethanol). Among them, ethers (for example, tetrahydrofuran (THF) and diethyl ether), carbonic acid diesters (for example, dimethyl carbonate and diethyl carbonate) and the like are preferably used. Although the reaction may use suitable mixed solvents, it is preferable to conduct the reaction in a solvent containing a carbonic acid diester.

The reaction temperature is usually about −20 to 200° C. and preferably about 15 to 90° C. The reaction time is usually about 0.1 to 100 hours and preferably about 1 to 50 hours.

The reaction shown in the above-mentioned (8) is conducted under, for example, the conditions described above.

A compound represented by the following formula:

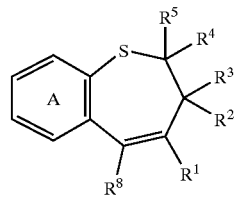

wherein each symbol is as defined above, or a salt thereof is prepared by subjecting a compound represented by the following formula:

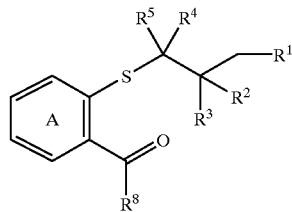

wherein each symbol is as defined above, or a salt thereof, to a ring-closing reaction.

The reaction shown in the above-mentioned (8) is preferably conducted in the presence of a base. Examples of such a base include metal hydrogen compounds (for example, hydrides of alkali metals such as sodium hydride and potassium hydride), metal hydrocarbons (for example, compounds having a chemical bond which combines $C_{1-4}$ alkyl with an alkali metal directly, such as n-butyllithium), alcoholates (for example, compounds which results from substitution of the hydrogen of a hydroxyl group of a $C_{1-4}$ alcohol with an alkali metal, such as NaOMe, NaOEt, t-BuONa, and t-BuOK), hydroxides of alkali metals (for example, NaOH and KOH), basic carbonates (for example, salts of alkali metals such as sodium salts and potassium salts, and alkaline earth metal salts such as calcium salts and magnesium salts), basic hydrogencarbonates (for example, hydrogencarbonates with alkali metal salts such as sodium salts and potassium salts), organic bases (for example, trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane and 1,8-diazabicyclo[5.4.0]-7-undecene). Metal hydrogen compounds (for example, sodium hydride and potassium hydride) and alcoholates (for example, NaOMe, NaOEt, t-BuONa, and t-BuOK) are desirably employed, and especially, alcoholates (for example, NaOMe, NaOEt, t-BuONa, and t-BuOK) are preferably employed.

The amount of the base used in the reaction of the above-mentioned (8) is about 0.1 to 100 equivalents, preferably about 1 to 5 equivalents.

Examples of solvents preferably employed include halogen-containing solvents (for example, methylene chloride, dichloroethane and chloroform), aliphatic hydrocarbons (for example, n-hexane), aromatic hydrocarbons (for example, benzene and toluene), ethers (for example, tetrahydrofuran (THF) and diethyl ether), polar solvents (for example, dimethylformamide (DMF) and dimethyl sulfoxide (DMSO)), carbonic acid diesters (for example, di-$C_{1-4}$ alkyl carbonates such as dimethyl carbonate and diethyl carbonate), formates (for example, $C_{1-4}$ alkyl formate), oxalic acid diesters (for example, di-$C_{1-4}$ alkyl oxalates), alcohols (for example, methanol, ethanol, propanol, isopropanol, n-butanol and 2-methoxyethanol). Among them, carbonic acid diesters (for example, dimethyl carbonate and diethyl carbonate) and the like are preferably used. Although the reaction may use suitable mixed solvents, it is preferable to conduct the reaction in a solvent containing a carbonic acid diester.

The reaction temperature is usually about −20 to 200° C. and preferably about 15 to 90° C. The reaction time is usually about 0.1 to 100 hours and preferably about 1 to 50 hours.

The reaction shown in the above-mentioned (15) is conducted under, for example, the conditions described above.

A compound represented by the following formula:

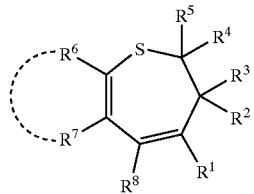

wherein each symbol is as defined above, or a salt thereof is prepared by causing a compound represented by the following formula:

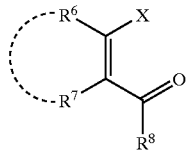

wherein each symbol is as defined above, or a salt thereof to react with a compound or a salt thereof:

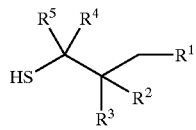

wherein each symbol is as defined above.

The reaction shown in the above-mentioned (15) is preferably conducted in the presence of a base. Examples of such a base include metal hydrogen compounds (for example, hydrides of alkali metals such as sodium hydride and potassium hydride), metal hydrocarbons (for example, compounds having a chemical bond which combines $C_{1-4}$ alkyl with an alkali metal directly, such as n-butyllithium), alcoholates (for example, compounds which results from substitution of the hydrogen of a hydroxyl group of a $C_{1-4}$ alcohol with an alkali metal, such as NaOMe, NaOEt, t-BuONa, and t-BuOK), hydroxides of alkali metals (for example, NaOH and KOH), basic carbonates (for example, salts of alkali metals such as sodium salts and potassium salts, and alkaline earth metal salts such as calcium salts and magnesium salts), basic hydrogencarbonates (for example, hydrogencarbonates with alkali metal salts such as sodium salts and potassium salts), organic bases (for example, trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane and 1,8-diazabicyclo[5.4.0]-7-undecene). Among them, metal hydrogen compounds (for example, sodium hydride and potassium hydride) and alcoholates (for example, NaOMe, NaOEt, t-BuONa, and t-BuOK) are desirably employed, and especially, alcoholates (for example, NaOMe, NaOEt, t-BuONa, and t-BuOK), particularly mixtures of potassium carbonate-alcoholate are preferably employed.

The amount of the base used in the reaction of the above-mentioned (15) is about 0.1 to 100 equivalents, preferably about 1 to 5 equivalents.

The reaction of the above-mentioned (15) may be conducted in the presence of a catalyst. Examples of such a catalyst include catalysts containing a transition metal such as nickel and palladium.

Examples of solvents preferably employed include halogen-containing solvents (for example, methylene chloride, dichloroethane and chloroform), aliphatic hydrocarbons (for example, n-hexane), aromatic hydrocarbons (for example, benzene and toluene), ethers (for example, tetrahydrofuran (THF) and diethyl ether), polar solvents (for example, dimethylformamide (DMF) and dimethyl sulfoxide (DMSO)), carbonic acid diesters (for example, di-$C_{1-4}$ alkyl carbonates such as dimethyl carbonate and diethyl carbonate), formates (for example, $C_{1-4}$ alkyl formates), oxalic acid diesters (for example, di-$C_{1-4}$ alkyl oxalates), alcohols (for example, methanol, ethanol, propanol, isopropanol, n-butanol and 2-methoxyethanol). Although the reaction may use suitable mixed solvents, it is preferable to conduct the reaction in a mixed solvent containing a carbonic acid diester and dimethylformamide.

The reaction temperature is usually about −20 to 200° C. and preferably about 15 to 90° C. The reaction time is usually about 0.1 to 100 hours and preferably about 1 to 50 hours.

Alternatively, the reaction of the above-mentioned (15) preferably proceeds through a compound represented by the following formula:

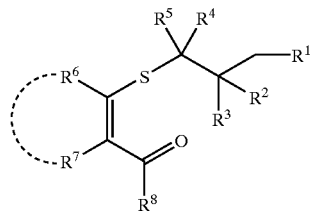

wherein each symbol is as defined below, or a salt thereof, as an intermediate. However, it is preferable to cause the reaction to proceed without isolation of the intermediate. When causing the reaction to proceed through the intermediate, it is also possible to cause the reaction to proceed by two steps, that is, the first step of forming the intermediate and the second step of closing the intermediate to form a ring by appropriately changing various reaction conditions (for example, the type and amount of a base, the presence or absence of a catalyst, the type of a solvent, the reaction temperature and the reaction time) wherein the first and second steps may be independent of each other and, alternatively, they also may partly overlap so that a part of the intermediates are closed to form rings during the first step. It is also possible to cause the reaction to proceed in one stage (one step) without any particular changes in reaction conditions. Furthermore, when it is necessary to form the intermediate intentionally, it is possible to form the intermediate by, for example, causing a step of forming the intermediate in the absence of an alcoholate (preferably in the presence of a basic carbonic acid salt; more preferably in the presence of potassium carbonate) and in the absence of a carbonic acid diester (preferably in the presence of a polar solvent; more preferably in the presence of dimethylformamide) to proceed, followed by causing a step of closing the intermediate to form a ring in the presence of an alcoholate (preferably in the co-presence of a basic carbonic acid salt; more preferably in the co-presence of potassium carbonate) and/or in the presence of a carbonic acid diester (preferably in the co-presence of a polar solvent; more preferably in the co-presence of dimethylformamide). Such an intermediate can be isolated, but it is preferable to conduct the reaction in a one pot without isolating the intermediate in either the case of causing the reaction to proceed in two stages or the case of causing the reaction to proceed in one stage.

On the other hand, the reaction shown in the above-mentioned (21) is conducted under, for example, the conditions described below.

A compound represented by the following formula:

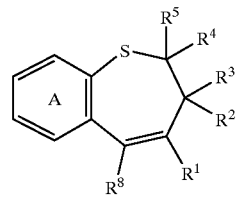

wherein each symbol is as defined above, or a salt thereof is prepared by causing a compound represented by the following formula:

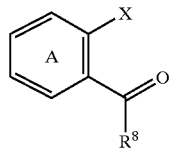

wherein each symbol is as defined above, or a salt thereof to react with a compound or a salt thereof:

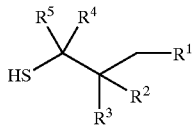

wherein each symbol is as defined above.

The reaction shown in the above-mentioned (21) is preferably conducted in the presence of a base. Examples of such a base include metal hydrogen compounds (for example, hydrides of alkali metals such as sodium hydride and potassium hydride), metal hydrocarbons (for example, compounds having a chemical bond which combines $C_{1-4}$ alkyl with an alkali metal directly, such as n-butyllithium), alcoholates (for example, compounds which results from substitution of the hydrogen of a hydroxyl group of a $C_{1-4}$ alcohol with an alkali metal, such as NaOMe, NaOEt, t-BuONa, and t-BuOK), hydroxides of alkali metals (for example, NaOH and KOH), basic carbonates (for example, salts of alkali metals such as sodium salts and potassium salts, and alkaline earth metal salts such as calcium salts and magnesium salts), basic hydrogencarbonates (for example, hydrogencarbonates with alkali metal salts such as sodium salts and potassium salts), organic bases (for example, trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane and 1,8-diazabicyclo[5.4.0]-7-undecene). Metal hydrogen compounds (for example, sodium hydride and potassium hydride) and alcoholates (for example, NaOMe, NaOEt, t-BuONa, and t-BuOK) are desirably employed, and especially, alcoholates (for example, NaOMe, NaOEt, t-BuONa, and t-BuOK), particularly mixtures of potassium carbonate-alcoholate are preferably employed.

The amount of the base used in the reaction of the above-mentioned (21) is about 0.1 to 100 equivalents, preferably about 1 to 5 equivalents.

The reaction of the above-mentioned (21) may be conducted in the presence of a catalyst. Examples of such a catalyst include catalysts containing a transition metal such as nickel and palladium.

Examples of solvents preferably employed include halogen-containing solvents (for example, methylene chloride, dichloroethane and chloroform), aliphatic hydrocarbons (for example, n-hexane), aromatic hydrocarbons (for example, benzene and toluene), ethers (for example, tetrahydrofuran (THF) and diethyl ether), polar solvents (for example, dimethylformamide (DMF) and dimethyl sulfoxide (DMSO)), carbonic acid diesters (for example, di-$C_{1-4}$ alkyl carbonates such as dimethyl carbonate and diethyl carbonate), formates (for example, $C_{1-4}$ alkyl formate), oxalic acid diesters (for example, di-$C_{1-4}$ alkyl oxalates), alcohols (for example, methanol, ethanol, propanol, isopropanol, n-butanol and 2-methoxyethanol). Although the reaction may use suitable mixed solvents, it is preferable to conduct the reaction in a mixed solvent containing a carbonic acid diester and dimethylformamide.

The reaction temperature is usually about −20 to 200 °C. and preferably about 15 to 90° C. The reaction time is usually about 0.1 to 100 hours and preferably about 1 to 50 hours.

Alternatively, the reaction of the above-mentioned (21) preferably proceeds through a compound represented by the following formula:

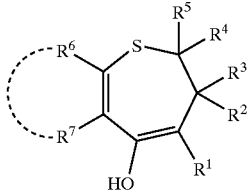

wherein each symbol is as defined above, or a salt thereof, as an intermediate. However, it is preferable to conduct the ring-closing reaction without isolation of the intermediate.

The reaction shown in the above-mentioned (27) is conducted under, for example, the conditions described below.

A compound represented by the following formula:

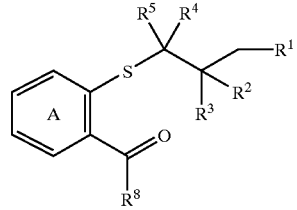

wherein each symbol is as defined above wherein this compound may have either an enol structure a keto structure, or a salt thereof, is prepared by subjecting a compound represented by the following formula:

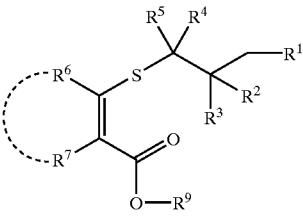

wherein each symbol is as defined above, or a salt thereof, to a ring-closing reaction in the presence of an alcoholate in a solvent containing a carbonic acid diester.

Examples of the alcoholate to be used in the reaction shown in the above-mentioned (27) include compounds resulting from substitution of hydrogen of hydroxyl groups of $C_{1-4}$ alcohols with alkali metals, such as NaOMe, NaOEt, t-BuONa and t-BuOK.

The amount of the alcoholate to be used in the reaction shown in the above-mentioned (27) is about 0.1 to 100 equivalents, preferably about 1 to 5 equivalents.

Examples of solvents preferably employed include halogen-containing solvents (for example, methylene chloride, dichloroethane and chloroform), aliphatic hydrocarbons (for example, n-hexane), aromatic hydrocarbons (for example, benzene and toluene), ethers (for example, tetrahydrofuran (THF) and diethyl ether), polar solvents (for example, dimethylformamide (DMF) and dimethyl sulfoxide (DMSO)), carbonic acid diesters (for example, di-$C_{1-4}$ alkyl carbonates such as dimethyl carbonate and diethyl carbonate), formates (for example, $C_{1-4}$ alkyl formate), oxalic acid diesters (for example, di-$C_{1-4}$ alkyl oxalates), alcohols (for example, methanol, ethanol, propanol, isopropanol, n-butanol and 2-methoxyethanol). Among them, carbonic acid diesters (for example, dimethyl carbonate and diethyl carbonate) and the like are preferably used. Although the reaction may use suitable mixed solvents, it is preferable to conduct the reaction in a solvent containing a carbonic acid diester.

The reaction temperature is usually about −20 to 200°0 C. and preferably about 15 to 90° C. The reaction time is usually about 0.1 to 100 hours and preferably about 1 to 50 hours.

The reaction shown in the above-mentioned (30) is conducted under, for example, the conditions described below.

A compound represented by the following formula:

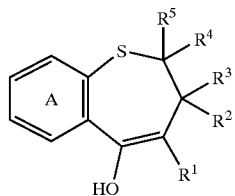

wherein each symbol is as defined above wherein this compound may have either an enol structure a keto structure, or a salt thereof, is prepared by subjecting a compound represented by the following formula:

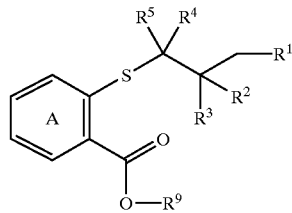

wherein each symbol is as defined above, or a salt thereof, to a ring-closing reaction in the presence of an alcoholate in a solvent containing a carbonic acid diester.

The reaction conditions of the reaction shown in the above-mentioned (30) may be, for example, reaction conditions the same as those of the reaction shown in the above-mentioned (27).

The reaction shown in the above-mentioned (37) is conducted under, for example, the conditions described above.

A compound represented by the following formula:

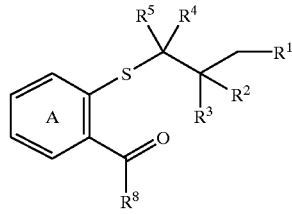

wherein each symbol is as defined above, or a salt thereof is prepared by causing a compound represented by the following formula:

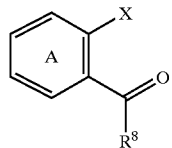

wherein each symbol is as defined above, or a salt thereof to react with a compound or a salt thereof:

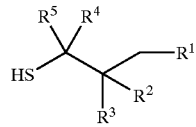

wherein each symbol is as defined above.

The reaction shown in the above-mentioned (37) is preferably conducted in the presence of a base. Examples of such a base include metal hydrogen compounds (for example, hydrides of alkali metals such as sodium hydride and potassium hydride), metal hydrocarbons (for example, compounds having a chemical bond which combines $C_{1-4}$ alkyl with an alkali metal directly, such as n-butyllithium), alcoholates (for example, compounds which results from substitution of the hydrogen of a hydroxyl group of a $C_{1-4}$ alcohol with an alkali metal, such as NaOMe, NaOEt, t-BuONa, and t-BuOK), hydroxides of alkali metals (for example, NaOH and KOH), basic carbonates (for example, salts of alkali metals such as sodium salts and potassium salts, and alkaline earth metal salts such as calcium salts and magnesium salts), basic hydrogencarbonates (for example, hydrogencarbonates with alkali metal salts such as sodium salts and potassium salts), organic bases (for example, trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane and 1,8-diazabicyclo[5.4.0]-7-undecene). Among them, basic carbonic acid salts (for example, carbonic acid salts of alkali metal salts sodium salts and potassium salts or alkaline earth metal salts such as calcium salts and magnesium salts) and the like, particularly potassium carbonate is preferably used.

The amount of the base used in the reaction of the above-mentioned (37) is about 0.1 to 100 equivalents, preferably about 1 to 5 equivalents.

The reaction of the above-mentioned (37) may be conducted in the presence of a catalyst. Examples of such a catalyst include catalysts containing a transition metal such as nickel and palladium.

Examples of solvents preferably employed include halogen-containing solvents (for example, methylene chloride, dichloroethane and chloroform), aliphatic hydrocarbons (for example, n-hexane), aromatic hydrocarbons (for example, benzene and toluene), ethers (for example, tetrahydrofuran (THF) and diethyl ether), polar solvents (for example, dimethylformamide (DMF) and dimethyl sulfoxide (DMSO)), carbonic acid diesters (for example, di-$C_{1-4}$ alkyl carbonates such as dimethyl carbonate and diethyl carbonate), formates (for example, $C_{1-4}$ alkyl formate), oxalic acid diesters (for example, di-$C_{1-4}$ alkyl oxalates), alcohols (for example, methanol, ethanol, propanol, isopropanol, n-butanol and 2-methoxyethanol). The reaction may use suitable mixed solvents, and particularly, dimethylformamide is preferably used.

The reaction temperature is usually about −20 to 200° C. and preferably about 15 to 90° C. The reaction time is usually about 0.1 to 100 hours and preferably about 1 to 50 hours.

The compound represented by the following formula:

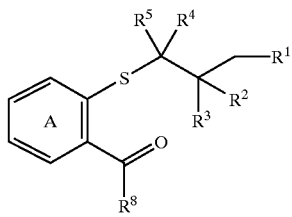

wherein R$^1$ is an electron-attracting group; R$^2$, R$^3$, R$^4$ and R$^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; ring A is an optionally substituted benzene ring; and R$^8$ is a hydrogen atom or an optionally substituted hydrocarbon group, or a salt thereof, wherein the compound or a salt thereof is obtained in the reaction shown in the above-mentioned (37), is a novel compound which has not been disclosed in any literature.

In the aforementioned formula, an optionally esterified carboxyl group is desirable as R$^1$, a hydrogen atom is desirable as R$^8$, and a hydrogen atom is desirable as R$^2$, R$^3$, R$^4$ and R$^5$.

Among the raw compounds to be used in the reaction shown in the above-mentioned (37), a compound represented by the following formula:

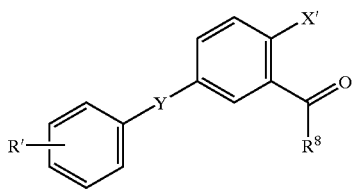

wherein X' represents a halogen atom, R$^8$ represents a hydrogen atom or an optionally substituted hydrocarbon group, Y represents a bond or a spacer, R' represents a C$_{1-4}$ alkoxy which may be substituted with a substituent selected from halogen atoms and C$_{1-4}$ alkoxy, or a salt thereof, is a novel compound which has not been disclosed in any literature.

Examples of the halogen atom represented by X' include fluorine, chlorine, bromine and iodine. Among the, fluorine is preferable. A hydrogen atom is preferably used as R$^8$.

Examples of the "spacer" represented by Y include divalent groups wherein the number of the atoms constituting their linear portion is from one to four, such as —(CH$_2$)$_a$— [a represents an integer of from 1 to 4, preferably an integer of from 1 to 2], —(CH$_2$)$_b$—X$^a$— [b represents an integer of from 0 to 3, preferably an integer of from 0 to 1, and X$^a$ represents an optionally substituted imino group (for example, an imino group which may be substituted with a lower (C$_{1-6}$) lower alkyl, a lower (C$_{3-7}$) cycloalkyl, formyl, a lower (C$_{2-7}$) lower alkanoyl, a lower (C$_{1-6}$) lower alkoxycarbonyl or the like), a carbonyl group, an oxygen atom or a sulfur atom which may be oxidized (for example, —S(O)$_n$— wherein n represents an integer of from 0 to 2)], —CH═CH—, —C≡C—, —CO—NH— and —SO$_2$—NH—. Preferred is —(CH$_2$)$_b$—X$^a$— and more preferred is —CH$_2$—O—. These divalent groups may be combined with a "benzene ring having a substituent X'" using either their right bonds or their left bond, but it is preferable to be combined with the "benzene ring having a substituent X'" through their right bonds. A bond or —CH$_2$—O— is preferably used as Y. A bond is more preferably used.

R' may substitute at any position and preferably substitutes at the para position. As R', ethoxy or propoxy is preferably employed.

A compound represented by the above-shown formula:

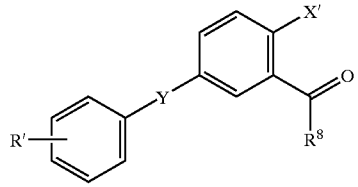

wherein each symbol is as defined above, or a salt thereof can be prepared by, for example, reaction (i), (ii) or methods according to them.

Reaction (i)

A compound represented by the following formula:

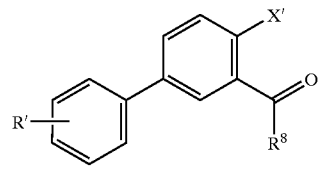

wherein each symbol is as defined below, or a salt thereof can be prepared by subjecting a compound represented by the following formula:

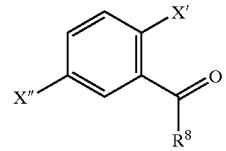

wherein X" represents a leaving group and each of the other symbol is as defined above, or a salt thereof, to substituted-phenylation using a compound represented by the following formula:

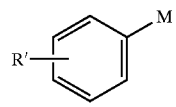

wherein M represents MgX, B(OH)$_2$, B(OR)$_2$ or SnR$_3$, X, R and R' are as defined above, or a salt thereof.

In one of the above formulas, examples of the leaving group represented by X" include halogen atoms (for example, fluorine, chlorine, bromine and iodine), groups represented by a formula —O(SO$_m$)R [in the formula, m represents 1 or 2, and R represents an optionally substituted hydrocarbon group (preferably C$_{1-4}$ alkyl which may be halogenated, and more preferably trifluoromethyl)]. Among them, preferred are halogen atoms. Particularly, iodine, bromine and the like are preferred.

This reaction may be conducted in the presence of a catalyst. Examples of such a catalyst include catalysts containing a transition metal such as nickel and palladium.

Dimethoxyethane, acetone, aromatic hydrocarbons (for example, benzene and toluene), ethers (for example, tetrahydrofuran (THF), diethyl ether and dioxane) and the like are used as a reaction solvent, but the reaction may use suitable mixed solvents. Moreover, water, alcohols (for example, methanol, ethanol, propanol, isopropanol, n-butanol and 2-methoxyethanol) or the like may appropriately coexist.

The reaction temperature is usually about −10 to 200° C. and preferably about 20 to 100° C. The reaction time is usually about 0.1 to 50 hours and preferably about 1 to 20 hours.

Reaction (ii)

A compound represented by the following formula:

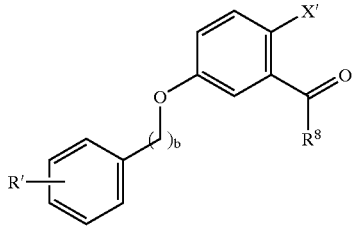

wherein each symbol is as defined below, or a salt thereof can be prepared by causing a compound represented by the following formula:

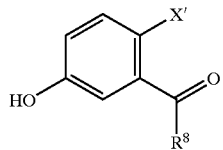

wherein each symbol is as defined above, or a salt thereof, to react with a compound represented by the following formula:

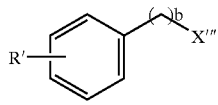

wherein X''' represents a leaving group, and b and R' are as defined above, or a salt thereof.

In one of the above formulas, examples of the leaving group represented by X''' include halogen atoms (for example, fluorine, chlorine, bromine and iodine), groups represented by a formula —O(SO$_m$)R [in the formula, m represents 1 or 2, and R represents an optionally substituted hydrocarbon group (preferably $C_{1-4}$ alkyl which may be halogenated, and more preferably trifluoromethyl)]. Among them, preferred are halogen atoms. Particularly, iodine, bromine, chlorine and the like are preferred.

This reaction is preferably conducted in the presence of a base. Examples of such a base include metal hydrogen compounds (for example, hydrides of alkali metals such as sodium hydride and potassium hydride), metal hydrocarbons (for example, compounds having a chemical bond which combines $C_{1-4}$ alkyl with an alkali metal directly, such as n-butyllithium), alcoholates (for example, compounds which results from substitution of the hydrogen of a hydroxyl group of a $C_{1-4}$ alcohol with an alkali metal, such as NaOMe, NaOEt, t-BuONa, and t-BuOK), hydroxides of alkali metals (for example, NaOH and KOH), basic carbonates (for example, salts of alkali metals such as sodium salts and potassium salts, and alkaline earth metal salts such as calcium salts and magnesium salts), basic hydrogencarbonates (for example, hydrogencarbonates with alkali metal salts such as sodium salts and potassium salts), organic bases (for example, trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2] octane and 1,8-diazabicyclo[5.4.0]-7-undecene).

The amount of the base used in this reaction is about 0.1 to 100 equivalents, preferably about 1 to 5 equivalents.

Examples of solvents preferably employed include halogen-containing solvents (for example, methylene chloride, dichloroethane and chloroform), aliphatic hydrocarbons (for example, n-hexane), aromatic hydrocarbons (for example, benzene and toluene), ethers (for example, tetrahydrofuran (THF) and diethyl ether), polar solvents (for example, dimethylformamide (DMF) and dimethyl sulfoxide (DMSO)), carbonic acid diesters (for example, di-$C_{1-4}$ alkyl carbonates such as dimethyl carbonate and diethyl carbonate), formates (for example, $C_{1-4}$ alkyl formate), oxalic acid diesters (for example, di-$C_{1-4}$ alkyl oxalates), alcohols (for example, methanol, ethanol, propanol, isopropanol, n-butanol and 2-methoxyethanol). The reaction may use suitable mixed solvents.

The reaction temperature is usually about −20 to 200° C. and preferably about 15 to 90° C. The reaction time is usually about 0.1 to 100 hours and preferably about 1 to 50 hours.

The compounds or their salts to be obtained by the reactions shown in the above-mentioned (1), (8), (15), (21), (27) and (30) themselves are useful as intermediates for synthesizing anilide derivatives disclosed in WO99/32100, WO99/32468, PCT/JP99/07148 and the like by condensing aniline derivative therewith in known methods.

For example, when a compound represented by the following formula:

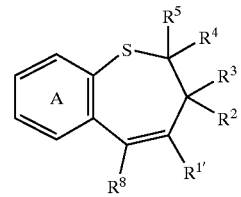

wherein $R^{1'}$ represents an esterified carboxyl group and each of the other symbols is as defined above, or a salt thereof, preferably a compound represented by the following formula:

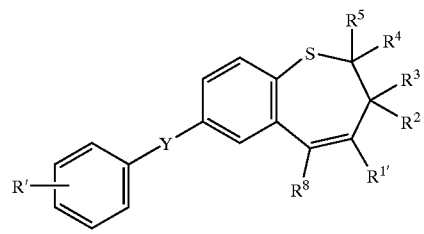

wherein each symbol is as defined above, or a salt thereof, is used as a raw material, a compound represented by the following formula:

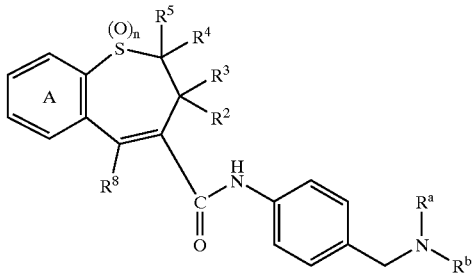

wherein each symbol is as defined above or below, or a salt thereof, preferably a compound represented by the following formula:

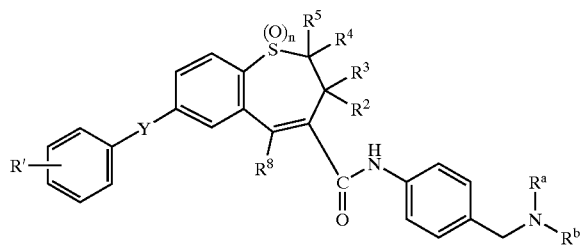

wherein each symbol is as defined above or below, or a salt thereof, can be prepared by subjecting, as demanded, the raw material to, for example, a reaction of converting an esterified carboxyl group as $R^{1'}$ to a carboxyl group and a reaction of oxidizing the sulfur atom in the thiepine ring according to known reactions (for example, a hydrolysis reaction of an ester and an oxidation reaction of a sulfur atom), followed by subjecting the resulting compound represented by the following formula:

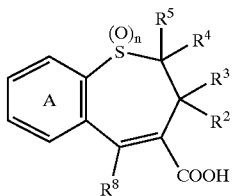

wherein each symbol is as defined above, a salt thereof or a reactive derivative thereof, preferably a compound represented by the following formula:

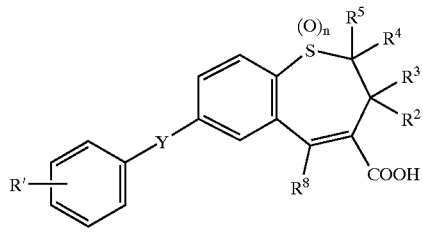

wherein each symbol is as defined above, a salt thereof or a reactive derivative thereof, to a condensation reaction with a compound represented by the following formula:

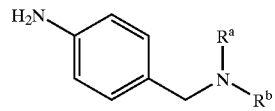

wherein $R^a$ and $R^b$, respectively, represent an optionally substituted hydrocarbon group or an optionally substituted heterocyclic group, or a salt thereof (for example, known condensation reactions disclosed in WO99/32100 and WO99/32468).

In the above formulas, examples of the "optionally substituted heterocyclic group" represented by $R^a$ and $R^b$ include those the same as the "optionally substituted heterocyclic group" represented by $R^2$, $R^3$, $R^4$, $R^5$, $R^6$ and $R^7$.

In the above formulas, as $R^a$, optionally substituted linear hydrocarbon groups (for example, optionally substituted alkyls and optionally substituted alkenyls) are preferable, optionally substituted lower $C_{1-6}$ alkyl groups are more preferable, and a methyl group is particularly preferable.

As $R^b$, optionally substituted alicyclic hydrocarbon groups (non-aromatic cyclic hydrocarbon groups) (for example, optionally substituted cycloalkyls and optionally substituted cycloalkenyls; preferably, optionally substituted lower $C_{3-8}$ cycloalkyl groups; more preferably, cyclohexyl) or optionally substituted alicyclic heterocyclic groups (non-aromatic heterocyclic groups) (preferably, optionally substituted saturated alicyclic heterocyclic groups (preferably 6-membered cyclic groups); more preferably, optionally substituted tetrahydropyranyl, optionally substituted tetrahydrothiopyranyl or optionally substituted piperidyl; particularly preferably, tetrahydropyranyl) are preferable.

The above-mentioned condensation reaction is conducted by the conventional peptide synthesis approach. The peptide synthesis approach can be conducted according to any known method, for example, the methods disclosed in M. Bodansky and M. A. Ondetti, "Peptide Synthesis", Interscience, New York, 1966; M. M. Finn and K. Hofmann, "The Proteins", Vol. 2, Edited by H. Nenrath and R. L. Hill, Academic Press Inc., New York, 1976; and Nobuo IZUMIYA, "Fundamentals and Experiments of Peptide Synthesis", Maruzen Co., Ltd., 1985, for example, an azide method, a chloride method, an acid anhydride method, a mixed acid anhydride method, a DCC method, an active ester method, a method using a Woodward reagent K, a carbonyldiimidazole method, an oxidation-reduction method, a DCC/HONB method, a WSC method and a method using diethyl cyanophosphate. This condensation reaction can be conducted in a solvent. Examples of such a solvent include anhydrous or hydrous N,N-dimethylformamide (DMF), dimethyl sulfoxide, pyridine, chloroform, dichloromethane, tetrahydrofuran (THF), dioxane, acetonitrile and appropriate mixtures of some of these solvents.

This condensation reaction usually uses about one to two moles of an amine compound per one mole of a carboxylic acid derivative. The reaction temperature is usually from about −20° C. to about 50° C., preferably from about −10° C. to about 30° C. The reaction time is from about one to about 100 hours, preferably from about 2 to about 40 hours. The anilide derivative thus obtained is can be isolated and purified by known separation purification means, such as concentration, vacuum concentration, solvent extraction, crystallization, recrystallization, redissolution and chromatography.

BEST MODE FOR CARRYING OUT THE INVENTION

The present invention will be described in more detail below with reference to Referential Examples and

EXAMPLES

Example 1

Production of methyl 4-(2-formylphenylthio) butyrate

Under an argon atmosphere, 2-fluorobenzaldehyde (3 g) was dissolved in 9 ml of dimethylformamide and potassium carbonate (5.01 g) was added. Methyl 4-mercaptobutyrate (4.5 ml) was added at room temperature and-was stirred at room temperature for 14 hours. After the addition of 50 ml of ethyl acetate, the mixture was washed with 30 ml of water twice, 3 ml of a 1N hydrochloric acid, and 30 ml of water three times. After drying with anhydrous sodium sulfate, the mixture was concentrated. The concentrated matter was subjected to silica gel chromatography (hexane/ethyl acetate=6/1) purification. The resulting effective fractions were concentrated to yield methyl 4-(2-formylphenylthio) butyrate (5.45 g, Yield 95%).

$^1$H-NMR (CDCl$_3$, δ, 300 MHz); 1.9–2.1 (2H, m), 2.51 (2H, t, J=7.1 Hz), 3.01 (2H, t, J=7.1 Hz), 3.68 (3H , s), 7.2–7.9 (4H, m), 10.36. (1H, s)

Example 2

Production of ethyl 4-(2-formylphenylthio)butyrate

Under an argon atmosphere, 2-fluorobenzaldehyde (5 g) was dissolved in 15 ml of dimethylformamide and potassium carbonate (8.35 g) was added. Ethyl 4-mercaptobutyrate (8.6 ml) was added at room temperature and was stirred at room temperature for 14 hours. After the addition of 100 ml of ethyl acetate, the mixture was washed with 50 ml of water twice, 50 ml of a 0.5N hydrochloric acid, and 50 ml of water three times. After drying with anhydrous sodium sulfate, the mixture was concentrated. The concentrated matter was subjected to silica gel chromatography (hexane/ethyl acetate=4/1) purification. The resulting effective fractions were concentrated to yield ethyl 4-(2-formylphenylthio)butyrate (6.86 g, Yield 67%).

$^1$H-NMR (CDCl$_3$, δ, 300 MHz); 1.26 (3H, t, J=7.1 Hz), 1.9–2.1 (2H , m) and 2.49 (2H, t, J=7.1 Hz), 3.01 (2H, t, J=7.1 Hz), 4.13 (2H, q, J=7.1 Hz), 7.2–7.9 (4H, m), 10.38. (1H, s)

Example 3

Production of methyl 2,3-dihydro-1-benzothiepine-4-carboxylate

Methyl 4-(2-formylphenylthio)butyrate (972 mg) was dissolved in 19 ml of dimethyl carbonate and a 28% sodium methoxide solution (1 ml) in methanol was dropped at room temperature. Stirring was conducted at room temperature for 17 hours. During cooling in ice, 7 ml of a 1N hydrochloric acid was added. Extraction with 20 ml of ethyl acetate was conducted. The organic layer was washed with 20 ml of water three times. After drying with anhydrous sodium sulfate, the mixture was concentrated. The concentrated matter was purified by silica gel chromatography (toluene). The resulting effective fractions were concentrated to yield methyl 2,3-dihydro-1-berzothiepine-4-carboxylate (637 mg, Yield 71%).

$^1$H-NMR (CDCl$_3$, δ, 300 MHz); 2.9–3.1 (2H, m), 3.1–3.3 (2H, m), 3.83 (3H, s), 7.1–7.5 (4H, m), 7.81. (1H, s)

Example 4

Production of ethyl 2,3-dihydro-1-benzothiepine-4-carboxylate

Ethyl 4-(2-formylphenylthio)butyrate (537 mg) was dissolved in 11 ml of diethyl carbonate and a 20% sodium ethoxide solution (1 ml) in ethanol was dropped at room temperature. Stirring was conducted at room temperature for 2 hours. During cooling in ice, 4 ml of a 1N hydrochloric acid was added. Extraction with 10 ml of ethyl acetate was conducted. The organic layer was washed with 20 ml of water three times. After drying with anhydrous sodium sulfate, the mixture was concentrated. The concentrated matter was purified by silica gel chromatography (toluene). The resulting effective fractions were concentrated to yield ethyl 2,3-dihydro-1-benzothiepine-4-carboxylate (352 mg, Yield 71%).

$^1$H-NMR (CDCl$_3$, δ, 300 MHz); 1.35 (3H, t, J=7.1 Hz), 2.9–3.0 (2H, m), 3.1–3.2 (2H, m), 4.28 (2H, q, J=7.1 Hz), 7.1–7.5 (4H, m), 7.81. (1H, s)

Example 5

Production of ethyl 2,3-dihydro-1-benzothiepine-4-carboxylate

Ethyl 4-(2-formylphenylthio)butyrate (537 mg) was dissolved in 6 ml of tetrahydrofuran and a suspension of 60% sodium hydride (102 mg) in 5 ml of tetrahydrofuran was dropped at room temperature. Stirring was conducted at room temperature for 1 hour. The mixture was stirred for 30 minutes under reflux. During cooling in ice, 4 ml of a 1N hydrochloric acid was added. Extraction with 10 ml of ethyl acetate was conducted. The organic layer was washed with 20 ml of water three times. The quantitative analysis by HPLC found 220 mg (Yield 44%) of ethyl 2,3-dihydro-1-benzothiepine-4-carboxylate and 28 mg (Yield 6.4%) of 2,3-dihydro-1-benzothiepine-4-carboxylic acid.

Example 6

Production of ethyl 7-(4-ethoxyphenyl)-2,3-dihydro-1-benzothiepine-4-carboxylate Under an argon atmosphere, 5-(4-ethoxyphenyl)-2-fluorobenzaldehyde (1.0 g) was dissolved in 2 ml of dimethylformamide and 1.17 g of potassium carbonate was added. Thereafter, 1.18 ml of ethyl 4-mercaptobutyrate was added and was stirred at room temperature for 25 hours. After addition of 20 ml of diethyl carbonate and an ethanol solution (2.8 g) of 20% sodium ethoxide, stirring was conducted at room temperature for three hours. During cooling in ice, 21 ml of a 1N hydrochloric acid was added. The mixture was extracted with 50 ml and additional 20 ml of ethyl acetate. The organic layers were combined and washed with 20 ml of water twice. The resulting organic layer was concentrated to yield crystals, which crystals were loosen in 2 ml of isopropyl alcohol added. The crystals were filtered out and were washed with 4 ml of isopropyl ether twice. After vacuum drying, ethyl 7-(4-ethoxyphenyl)-2,3-dihydro-1-benzothiepine-4-carboxylate (0.8 g, Yield 57%) was obtained.

$^1$H-NMR (CDCl$_3$, δ, 300 MHz); 1.3–1.5 (6H, m), 2.9–3.1 (2H, m), 3.1–3.3 (2H, m), 4.07 (2H, q, J=7.0 Hz), 4.29 (2H, q, J=7.0 Hz), 6.9–7.0 (2H, m), 7.3–7.6 (5H, m), 7.86. (1H, s)

Referential Example 1

Production of 5-(4-ethoxyphenyl)-2-fluorobenzaldehyde

Under an argon atmosphere, tetrakistriphenylphosphine palladium (69 mg) was added to 5 ml of 1,2- dimethoxyethane. A mixture resulting from dissolving 5-bromo-2-fluorobenzaldehyde (406 mg) in 5 ml of 1,2-dimethoxyethane was added. A mixture resulting from dissolving 4-ethoxyphenylboric acid (398 mg) in 1.5 ml of 1,2-dimethoxyethane was added. Two milliliter of 2M sodium carbonate solution was added. Stirring was conducted for one hour and ten minutes under reflux. After cooling to room temperature, 20 ml of toluene was added and was washed with 10 ml of water twice, 10 ml of a 2N sodium hydroxide solution twice and 10 ml of water twice. After drying with anhydrous sodium sulfate, the mixture was concentrated. The concentrated matter was purified by silica gel chromatography (hexane/ethyl acetate=4/1). The resulting effective fractions were concentrated to yield 5-(4-ethoxyphenyl)-2-fluorobenzaldehyde (369 mg, Yield 76%).

$^1$H-NMR (CDCl$_3$, δ, 300 MHz); 1.44 (3H, t, J=7.0 Hz), 4.08 (2H, q, J=7.0 Hz), 6.9–7.0 (2H, m), 7.1–7.3 (1H, m), 7.4–7.5 (2H, m), 7.7–7.8 (1H, m), 8.0–8.1 (1H, m), 10.41 (1H, s).

Referential Example 2

Production of 5-(4-ethoxyphenyl)-2-fluorobenzaldehyde

Under an argon atmosphere, magnesium (1.25 g, 51.5 mmol) was suspended in 100 ml of tetrahydrofuran, which was then refluxed. Under reflux, 50 ml of a tetrahydrofuran solution of bromophenetole (10 g, 50 mmol) was dropped and refluxed for 2 hours. After cooling to −11° C., a solution of trimethoxyborane (5.6 ml, 50 mmol) in 50 ml of tetrahydrofuran was dropped at −11 to −8° C. Stirring was conducted at −10° C. for 1 hour. At room temperature, palladium (II) acetate (64 mg, 0.285 mmol) and subsequently triphenylphosphine (299 mg, 1.14 mmol) were added and stirred at room temperature for 30 minutes. 5-Bromo-2-fluorobenzaldehyde (5.79 g, 28.5 mmol) and subsequently 30 ml of an aqueous solution of potassium carbonate (20.7 g, 150 mmol) were added at room temperature and heated under reflux for 5 hours. After cooling to room temperature, 170 ml of a 2N hydrochloric acid was dropped at 20 to 30° C. After phase separation had occurred, the water layer was extracted with 80 ml of toluene. The organic layers were combined and washed with two 100-ml portions of saturated brine. To the organic layer, 1.0 g of activated carbon (Shirasagi A) and tri-n-butylphosphine (0.71 ml) were added and stirred at 70° C. for 20 minutes. After filtration, the residue was washed with 50 ml of toluene and then the filtrate was concentrated under vacuum. Ten milliliters of ethanol was added and then 5 ml of water was added under reflux. After cooling, the resultant was stirred while cooling in ice. The resultant was filtered under reduced pressure and the residue was washed with 20 ml of ethanol containing 50% of water. The residue was dried under vacuum (40° C.) to yield 5.7 g (Yield 82%) of 5-(4-ethoxyphenyl)-2-fluorobenzaldehyde.

Example 7

Production of ethyl 4-(4-bromo-2-formylphenylthio)butyrate

Ethyl 4-(4-bromo-2-formylphenylthio)butyrate was synthesized from 5-bromo-2-fluorobenzaldehyde and ethyl 4-mercaptobutyrate in the same manner as Example 2. After column chromatography, crystallization from hexane/isopropyl ether yielded ethyl 4-(4-bromo-2-formylphenylthio)butyrate (Yield 78%) as yellow crystals.

$^1$H-NMR (CDCl$_3$, δ, 300 MHz); 1.26 (3H, t, J=7.14 Hz), 1.95–2.05 (2H, m), and 2.48 (2H, t, J=7.08 Hz), 3.00 (2H, t, J=7.20 Hz), 4.13 (2H, q, J=7.14 Hz), 7.35 (1H, d, J=8.49 Hz), 7.60–7.64 (1H, m), 7.94 (1H, d, J=2.31 Hz), 10.32(1H, s)

Example 8

Production of ethyl 4-(4-(4-ethoxyphenyl)-2-formylphenylthio)butyrate

Ethyl 4-(4-(4-ethoxyphenyl)-2-formylphenylthio)butyrate was synthesized from 5-(4-ethoxyphenyl)-2-fluorobenzaldehyde and ethyl 4-mercaptobutyrate in the same manner as Example 2. After concentration of an extracted solution, crystallization from hexane/isopropyl ether yielded ethyl 4-(4-(4-ethoxyphenyl)-2-formylphenylthio)butyrate (Yield 73%) as yellow crystals.

$^1$H-NMR (CDCl$_3$, δ, and 300 MHz); 1.26 (3H, t, J=7.11 Hz), 1.44 (3H, t, J=6.99 Hz), 2.00–2.06 (2H, m), 2.50 (2H, t, J=7.17 Hz), 3.04 (2H, t, J=7.11 Hz), 4.05–4.18 (4H, m), 6.96–6.99 (2H, m), 7.50–7.56 (3H, m), 7.70–7.73 (1H, m), 8.02–8.04 (1H, m), 10.46(1H, s)

Example 9

Production of ethyl 4-(2-chloro-6-formylphenylthio)butyrate

Ethyl 4-(2-chloro-6-formylphenylthio)butyrate was synthesized from 2,3-dichlorobenzaldehyde and ethyl 4-mercaptobutyrate in the same manner as Example 2. After column chromatography, vacuum concentration yielded ethyl 4-(2-chloro-6-formylpehylthio)butyrate (Yield 70%) as a yellow oily matter.

$^1$H-NMR (CDCl$_3$, δ, 300 MHz); 1.26 (3H, t, J=7.18 Hz), 1.84–1.94 (2H, m), 2.43 (2H, t, J=7.23 Hz), 2.95 (2H, t, J=7.20 Hz), 4.11 (2H, q, J=7.18 Hz), 7.42 (1H, dd, J=7.71, 7.23 Hz), 7.71 (1H, d, J=7.94 Hz), 7.84 (1H, d, J=7.74 Hz), 10.77(1H, s)

Example 10

Production of ethyl 4-(3,4-dimethoxy-6-formylphenylthio)butyrate

Ethyl 4-(3,4-dimethoxy-6-formylphenylthio)butyrate was synthesized from 6-bromoveratraldehyde and ethyl 4-mercaptobutyrate in the same manner as Example 2. After vacuum concentration of an extracted solution, the residue was crystallized from isopropyl ether to yield ethyl 4-(3,4-dimethoxy-6-formylphenylthio)butyrate (Yield 27%) as slightly yellow crystals.

$^1$H-NMR (CDCl$_3$, δ, 300 MHz); 1.24 (3H, t, J=7.14 Hz), 1.80–2.07 (2H, m), and 2.43 (2H, t, J=7.05 Hz), 2.92 (2H, t, J=7.41 Hz), 3.93 (3H,s), 3.99 (3H,s), 4.12 (2H, q, J=7.14 Hz), 7.02 (1H,s), 7.41 (1H, s), 10.48(1H,s)

Example 11

Production of ethyl 7-bromo-2,3-dihydro-1-benzothiepine-4-carboxylate

Ethyl 7-bromo-2,3-dihydro-1-benzothiepine-4-carboxylate was synthesized from ethyl 4-(4-bromo-2-formylphenylthio)butyrate in the same manner as Example 4. Using diethyl carbonate as a solvent and an ethanol solution of 20% sodium ethoxide as a base, ethyl 7-bromo-2,3-dihydro-1-benzothiepine-4-carboxylate was obtained as yellow crystals (Yield 32%).

¹H-NMR (CDCl₃, δ, 300 MHz); 1.35 (3H, t, J=7.14 Hz), 2.95–2.99 (2H, m), 3.15–3.20 (2H, m), 4.28 (2H, q, J=7.14 Hz), 7.26–7.34 (2H, m), 7.51–7.52 (1H, m), 7.69(1H, s)

Example 12

Production of ethyl 7-(4-ethoxyphenyl)-2,3-dihydro-1-benzothiepine-4-carboxylate Ethyl 7-(4-ethoxyphenyl)-2,3-dihydro-1-benzothiepine-4-carboxylate was synthesized from ethyl 4-(4-(4-ethoxyphenyl)-2-formylphenylthio)butyrate in the same manner as Example 4. Using diethyl carbonate as a solvent and an ethanol solution of 20% sodium ethoxide as a base, ethyl 7-bromo-2,3-dihydro-1-benzothiepine-4-carboxylate was obtained as yellow crystals (Yield 73%) by concentration of an extracted solution and subsequent crystallization from isopropyl ether.

¹H-NMR (CDCl₃, δ, 300 MHz); 1.34 (3H, t, J=7.17 Hz), 1.44 (3H, t, J=6.96 Hz), 2.97–3.02 (2H, m), 3.19–3.24 (2H, m), 4.07 (2H, q, J=6.96 Hz), 4.29 (2H, q, J=7.17 Hz), 6.96 (2H, d, J=8.70 Hz), 7.36–7.56 (5H, m), 7.87(1H, s)

Example 13

Production of ethyl 7,8-dimethoxy-2,3-dihydro-1-benzothiepinecarboxylate

Ethyl 7-bromo-2,3-dihydro-1-benzothiepine-4-carboxylate was synthesized from ethyl 4-(3,4-dimethoxy-6-formylphenylthio)butyrate in the same manner as Example 4. Using diethyl carbonate as a solvent and an ethanol solution of 20% sodium ethoxide as a base, ethyl 7,8-dimethoxy-2,3-dihydro-1-benzothiepinecarboxylate was obtained as an yellow oily matter (Yield 70%).

¹H-NMR (CDCl₃, δ, 300 MHz); 1.35 (3H, t, J=7.11 Hz), 2.95–2.98 (2H, m), 3.16–3.21 (2H, m), 3.88 (3H, s), 3.89 (3H, s), 4.28 (2H, q, J=7.11 Hz), 6.86 (1H, s), 6.96 (1H, s), 7.74(1H, s)

Example 14

Production of ethyl 9-chloro-2,3-dihydro-1-benzothiepine-4-carboxylate

Ethyl 9-chloro-2,3-dihydro-1-benzothiepine-4-carboxylate was synthesized from ethyl (2-chloro-6-formylpehylthio)butyrate in the same manner as Example 4. Using diethyl carbonate as a solvent and an ethanol solution of 20% sodium ethoxide as a base, ethyl 9-chloro-2,3-dihydro-1-benzothiepine-4-carboxylate was obtained as yellow crystals (Yield 46%).

¹H-NMR (300 MHz, CDCl₃, δ) ; 1.35 (3H, t, J=7.12 Hz), 2.99–3.03 (2H, m), 3.15–3.20 (2H, m), 4.28 (2H, q, J=7.12 Hz), 7.12–7.27 (1H, m), 7.26–7.36 (2H, m), 7.77(1H, s)

Referential Example 3

Production of p-bromopropoxybenzene

Bromophenol (996 g, 5.76 mmol), bromopropane (790 ml, 8.70 mmol) and tetrabutylammonium hydrogensulfate (19.6 g, 48.9 mmol) were dissolved slowly in 5 L of dimethyl sulfoxide. A solution resulting from dissolving sodium hydroxide (2300 g, 57.6 mmol) in 2300 g of water was dropped slowly. Since heat was generated during the above operation, the solution was added so that the internal temperature was kept at 40–45° C. After stirring at room temperature for 1 hour, the mixture was cooled to 25° C. and then 6.7 L of water was added while keeping at 20–30° C. After addition of 12 L of toluene, 3 L of tetrahydrofuran and 3.3 L of water, phase separation was conducted. The organic layer was washed with 8 L of water, two 4.2 L portions of a 20% brine and 8 L of water. After vacuum concentration, the residue was distilled under reduced pressure to yield p-bromopropoxybenzene (b.p. 96–100° C./4 mmHg, 1182.5 g, Yield 95.5%) as a colorless oily matter.

¹H-NMR (CDCl₃, δ, 300 MHz); 1.01 (3H, t, J=7.41 Hz), 1.72–1.84 (2H, m), 3.85 (2H, t, J=6.57 Hz), 6.73–6.79 (2H, m), 7.31–7.37(2H, m)

Referential Example 4

Production of 2-fluoro-5-(4-propoxyphenyl) benzaldehyde

Under an argon atmosphere, magnesium (4311 mg, 177.34 mmol) was suspended in 270 ml of tetrahydrofuran, which was then refluxed. Under reflux, 90 ml of a tetrahydrofuran solution of p-bromopropoxybenzene (37.08 g, 172.41 mmol) was dropped and refluxed for 1.5 hours. After cooling to −11° C., a solution of trimethoxyborane (17.92 ml, 172.41 mmol) in 90 ml of tetrahydrofuran was dropped at −11 to −8° C. Stirring was conducted at −10° C. for 1 hour. At room temperature, palladium (II) acetate (11 mg, 0.04926 mmol) and subsequently triphenylphosphine (52 mg, 0.1970 mmol) were added and stirred at room temperature for 30 minutes. 5-Bromo-2-fluorobenzaldehyde (20 g, 98.52 mmol) and subsequently 85 ml of an aqueous solution of potassium carbonate (71.49 g, 517.23 mmol) were added at room temperature and heated under reflux for 4 hours. After cooling to room temperature, 450 ml of a 2N hydrochloric acid was dropped at 20 to 30° C. After phase separation had occurred, the water layer was extracted with 450 ml of toluene. The organic layers were combined and washed with 300 ml of a 2N hydrochloric acid, two 300-ml portions of a 2N sodium hydroxide, 300 ml of a 20% brine, 300 ml of a 2N hydrochloric acid and two 300-ml portions of a 20% brine. To the organic layer, 1.0 g of activated carbon (Shirasagi A) was added and stirred at room temperature for 20 minutes. After filtration, the residue was washed with 50 ml of toluene and then the filtrate was concentrated under vacuum, resulting in 30.5 g of crude 2-fluoro-5-(4-propoxyphenyl)benzaldehyde as a brown oily matter, which was used in the next step without being purified. A part of the product was purified by column chromatography to yield 2-fluoro-5-(4-propoxyphenyl)benzaldehyde as white crystals.

¹H-NMR (CDCl₃, δ, 300 MHz); 1.06 (3H, t, J=7.38 Hz), 1.77–1.90 (2H, m), 3.96 (2H, t, J=6.60 Hz), 6.95–6.98 (2H, m), 7.13–7.25 (1H, m), 7.46–7.50 (2H, m), 7.74–7.78 (1H, m), 8.00–8.04 (1H, m), 10.41(1H, s)

Example 15

Production of ethyl 7-(4-propoxyphenyl)-2,3-dihydro-1-benzothiepine-4-carboxylate Under an argon flow, 30.5 g of crude 2-fluoro-5-(4-propoxyphenyl)benzaldehyde was dissolved in 59 ml of DMF and then cooled to 5° C. After the addition of ethyl 4-mercaptobutyrate (32.6 ml, 229.88 mmol), 1,8-diazabicyclo[5.4.0]-7-undecene (34.4 ml, 229.88 mmol) was dropped slowly, while keeping at 0–10° C. The mixture was heated to 20° C. and stirred at 20–30° C. for 3 hours. At 20–30° C., 590 ml of diethyl carbonate was dropped and subsequently an ethanol solution (156 g, 459.76 mmol) of 20% sodium ethoxide was dropped. After stirring at 20–30° C. for 3 hours, the mixture was cooled to 5° C. After adding 338 ml of a 2N hydrochloric acid while keeping 10° C. or lower, phase separation was conducted. The water layer was extracted with 290 ml of ethyl acetate. The organic layers were combined and washed with 300 ml of water, 300 ml of a 5% aqueous sodium hydrogencarbonate solution and 300 ml of a 5% brine. After the addition of activated carbon, Shirasagi A (3.5 g), followed by the addition of tri-n-butylphosphine (4 ml), the mixture was stirred at room temperature for 20 minutes. After filtration, the residue was washed with 60 ml of ethyl acetate and the filtrate was concentrated under reduced pressure. After addition of 60 ml of isopropyl alcohol, the mixture was concentrated under reduced pressure. Subsequently, 60 ml of isopropyl ether was added and stirred at room temperature. The crystals formed were dissolved on heating under reflux. The solution was cooled for 1.5 hours while being stirred and subsequently stirred for 2 hours while being cooled in ice. After filtration, the residue was washed with 60 ml of ice-cooled isopropyl ether and then dried under vacuum (40° C.), yielding 20.34 g of ethyl 7-(4-propoxyphenyl)-2,3-dihydro-1-benzothiepine-4-carboxylate as pale yellow crystals (Yield from 5-bromo-2-fluorobenzaldehyde 48%).

$^1$H-NMR (CDCl$_3$, δ, 300 MHz); 1.06 (3H, t, J=7.40 Hz), 1.36 (3H, t, J=7.11 Hz), 1.77,–1.90 (2H, m), 3.00 (2H, t, J=5.27 Hz), 3.22 (2H, t, J=5.60 Hz), 3.96 (2H, t, J=6.59 Hz), 4.29 (2H, q, J=7.11 Hz), 6.94–7.00 (2H, m), 7.36–7.57 (5H, m), 7.87(1H,s)

Referential Example 5

Production of ethyl 7-(4-propoxyphenyl)-1,1-dioxo-2,3-dihydro-1-benzothiepine-4-carboxylate Ethyl 7-(4-propoxyphenyl)-2,3-dihydro-1-benzothiepine-4-carboxylate (15 g, 40.707 mmol) was suspended in 135 ml of acetic acid and was heated to 56° C. to dissolve. A solution of 30% hydrogen peroxide (9.5 g, 83.449 mmol) in 15 ml of acetic acid was dropped slowly and then was stirred at 65–70° C. for 3 hours. At that temperature, 60 ml of an aqueous sodium sulfite solution was dropped and disappearance of the peroxide was checked with iodo-starch paper. At that temperature, 15 ml of water was dropped. Crystals were formed and the mixture was cooled and stirred for 2 hours. After filtration, the residue was washed with 15 ml of a mixed solution of acetic acid/water =3/2 and subsequently with 150 ml of water. After vacuum drying (40° C.), 15.4 g (Yield 94%) of ethyl 7-(4-propoxyphenyl)-1,1-dioxo-2,3-dihydro-1-benzothiepine-4-carboxylate was obtained as white crystals.

$^1$H-NMR (CDCl$_3$, δ, 300 MHz); 1.06 (3H, t, J=7.42 Hz), 1.38 (3H, t, J=7.17 Hz), 1.78,–1.90 (2H, m), 3.14 (2H, t, J=6.31 Hz), 3.64 (2H, t, J=7.08 Hz), 3.98 (2H, t, J=6.55 Hz), 4.32 (2H, q, J=7.17 Hz), 6.99–7.02 (2H, m), 7.53–7.57 (2H, m), 7.65–7.69 (2H, m), 7.89 (1H, s), 8.18(1H, d, J=7.97 Hz)

Referential Example 6

Production of 7-(4-propoxyphenyl)-1,1-dioxo-2,3-dihydro-1-benzothiepine-4-carboxylic acid Ethyl 7-(4-propoxyphenyl)-1,1-dioxo-2,3-dihydro-1-benzothiepine-4-carboxlate (495 g, 1.24 mol) was dissolved in 4.95 L of tetrahydrofuran and 2.48 L of methanol. Crystals were formed by adding a potassium carbonate (342 g, 2.47 mol) solution in 4.2 L of water and the mixture was heated under reflux for 6.5 hours. Under reflux, 1.85 L of a 3N hydrochloric acid was dropped to form crystals. After cooling, 84 ml of a 6N hydrochloric acid was added at room temperature (pH 2–3) and stirred for 1 hour while cooling in ice. After filtration, the residue was washed with 2.97 L of a mixed solution of tetrahydrofuran/methanol/water=1/1/3 . After vacuum drying (40° C.), 443 g (Yield 96%) of 7-(4-propoxyphenyl)-1,1-dioxo-2,3-dihydro-1-benzothiepine-4-carboxylic acid was obtained as pale yellowish white crystals.

$^1$H-NMR (DMSO, δ, 300 MHz); 0.98 (3H, t, J=7.36 Hz), 1.70–1.78 (2H, m), 2.95 (2H, t, J=6.22 Hz), 3.73 (2H, t, J=6.41 Hz), 3.98 (2H, t, J=6.50 Hz), 7.05 (2H, d, J=8.74 Hz), 7.75 (2H, d, J=8.74 Hz), 7.86–7.88 (2H, m), 8.02–8.05 (2H, m)

Referential Example 7

Production of 7-(4-propoxyphenyl)-1,1-dioxo-2,3-dihydro-1-benzothiepine-4-carboxylic acid Ethyl 7-(4-propoxyphenyl)-1,1-dioxo-2,3-dihydro-1-benzothiepine-4-carboxlate (1.0 g, 2.497 mmol) was dissolved in 15 ml of a mixed solution of tetrahydrofuran/ethylene glycol =2/1. Crystals were formed by adding 8.5 ml of water. Potassium carbonate (690 mg, 4.994 mmol) was added and the mixture was heated under reflux for 3.25 hours. Under reflux, 3.5 ml of a 3N hydrochloric acid was dropped to form crystals. After cooling, the mixture was stirred at 20–30° C. for 45minutes and for 1 hour while cooling in ice. After filtration, the residue was washed with 10 ml of a mixed solution of tetrahydrofuran/methanol/water=1/1/3. After vacuum drying (40° C.), 858 mg (Yield 92%) of 7-(4-propoxyphenyl)-1, 1-dioxo-2,3-dihydro-1-benzothiepine-4-carboxylic acid was obtained as pale yellowish white crystals.

Referential Example 8

Production of N-[4-[N-methyl-N-(tetrahydropyran-4-yl)aminomethyl]phenyl]-7-(4-propoxyphenyl)-1,1-dioxo-2,3-dihydro-1-benzothiepine-4-carboxamide 7-(4-Propoxyphenyl)-1,1-dioxo-2,3-dihydro-1-benzothiepine-4-carboxlic acid (2.0 g, 5.37 mmol) was suspended in 10 ml of N,N-dimethylacetamide and thionyl chloride (703 mg, 5.907 mmol) was added at room temperature. After stirring at room temperature for 2 hours, an acid chloride solution was obtained as a homogeneous solution. 4-[N-methyl-N-(tetrahydropyran-4-yl) aminomethyl]aniline dihydrochloride (1890 mg, 6.444 mmol) was suspended in 30 ml of N,N-dimethylacetamide and triethylamine (5.84 ml, 41.886 mmol) was added at room temperature, followed by being stirred at room temperature for 1 hour. During cooling of the mixture in ice, the acid chloride solution previously obtained was dropped at 0–10° C. and was stirred at room temperature for 1 hour. Twenty milliliter of water was dropped slowly and stirred at room temperature for 1 hour and 15 minutes. Crystals were filtered and then washed with water and methanol. After vacuum drying, 2.58 g (Yield 82%) of N-[4-[N-methyl-N-(tetrahydropyran-4-yl)aminomethyl]phenyl]-7-(4-propoxyphenyl)-1,1-dioxo-2,3-dihydro-1-benzothiepine-4-carboxamide was obtained as white crystals.

$^1$H-NMR(CDCl$_3$, δ, 300 MHz); 1.06 (3H, t, J=7.43 Hz), 1.64–1.88 (6H, m), 2.20 (3H, s), 2.60–2.67 (1H, m), 3.13 (2H, t, J=6.61 Hz), 3.33–3.41 (2H, m), 3.56 (2H, s), 3.69 (2H, t, J=6.34 Hz), 3.95–4.07 (4H, m), 6.98 (2H, d, J=8.71 Hz), 7.29–7.34 (3H, m), 7.48–7.61 (6H, m), 8.08–8.16(2H, m)

Referential Example 9

Production of p-bromophenoxyethanol

Phenoxyethanol (440 g, 3.1874 mol) was dissolved in 880 ml of a mixed solution of acetic acid/water =7/3. Sodium acetate (340 g, 4.1436 mol) was added and cooled to 15° C. A solution resulting from dissolving bromine (514.5 g, 3.22 mol) in 1760 ml of a mixed solution of acetic acid/water=7/3 was dropped while keeping at 15–20° C. and then was stirred at 10–20° C. for 30 minutes. Yellow color remained a little. Six milliliter of a 10 W/W% aqueous sodium sulfite solutions was dropped. The mixture became colorless. Dropping 2200 ml of water caused clouding. Crystallization was conducted by addition of seed crystals and stirring at room temperature for 30 minutes. After adding 4400 ml of water, stirring was done at room temperature for 30 minutes and at 0–10° C. for 1.5 hours. The crystals were filtered and washed with 3 L of water. After overnight air-drying and vacuum drying (35–40° C.) for 16 hours, 631 g (Yield 91.3%) of p-bromophenoxyethanol was obtained as white crystals.

$^1$H-NMR (CDCl$_3$, δ, 300 MHz); 2.13 (1H, s), 3.95–3.98 (2H, m), 4.03–4.06 (2H, m), 6.77–6.82 (2H, m), 7.35–7.40 (2H, m)

Referential Example 10

Production of 1-p-bromophenoxy-2-propoxyethane p-Bromophenoxyethanol (2067 g, 9.5227 mol), bromopropane (2342 g, 19.05 mol) and tetrabuthylammonium hydrogensulfate (162 g, 0.476 mol) were dissolved in 10.3 L of dimethyl sulfoxide. A 50 W/W% aqueous sodium hydroxide solution (3.81 kg, 47.625 mol) was dropped slowly. Since heat was generated, the dropping rate and the external temperature were adjusted so that the internal temperature was kept at 40–50° C. After cooling and stirring for 1.5 hours, the mixture was cooled to 20–30° C. and 20.6 L of water was added at that temperature. After addition of 15.5 L of toluene and 4 L of tetrahydrofuran, phase separation was conducted. To the water layer, 5.2 L of toluene 5.2 L and t1.3 L of tetrahydrofuran and extraction was conducted. The organic layers were combined and washed with 20.6 L of water, two 10.3-L portions of 20% brine, two 20.6-L portions of water. After vacuum concentration, the residue was distilled under reduced pressure (135–155° C. /5 mmHg) to yield 2412.8 g (Yield 98%) of 1-p-bromophenoxy-2-propoxyethane as a colorless oily matter.

$^1$H-NMR (CDCl$_3$, δ, 300 MHz); 0.93 (3H, t, J=7.41 Hz), 1.56–1.69 (2H, m), 3.48 (2H, t, J=6.75 Hz), 3.74–3.78 (2H, m), 4.06–4.09 (2H, m), 6.77–6.83 (2H, m), 7.32–7.38(2H, m)

Referential Example 11

Production of 2-fluoro-5-(4-propoxyethoxyphenyl) benzaldehyde

Under an argon atmosphere, magnesium (737 mg, 30.299 mmol) was suspended in 40.5 ml of tetrahydrofuran, which was then refluxed. Under reflux, a solution of 1-p-bromophenoxy-2-propoxyethane (7.66 g, 29.56 mmol) in 13.5 ml of tetrahydrofuran was dropped and refluxed for 1.5 hours. After cooling to room temperature, the resultant sealed was stored in a refrigerator to form seeds. Under a nitrogen flow, magnesium (73.7 g, 3.0299 mol) was suspended in 4050 ml of tetrahydrofuran, which was then refluxed. Under reflux, the seeds previously prepared were added. A solution of 1-p-bromophenoxy-2-propoxyethane (766 g, 2.956 mol) in 1350 ml of tetrahydrofuran was dropped. After refluxing for 3 hours, the mixture was cooled to 14° C. A solution of trimethoxyborane (310 g, 2.99 mmol) in 1350 ml of tetrahydrofuran was dropped at −15 to −10° C. and stirred at −15 to −10° C. for 1 hour. The mixture was heated to room temperature, sealed and left stand overnight. Under a nitrogen flow, palladium (II) acetate (3318 mg, 14.78 mmol) and subsequently triphenylphosphine (15.506 g, 59.12 mmol) were added at room temperature and stirred at room temperature for 30 minutes. 5-Bromo-2-fluorobenzaldehyde (300 g, 1.478 mmol) and subsequently 1275 ml of an aqueous solution of potassium carbonate (1072 g, 7.76 mol) were added at room temperature and was heated under reflux for 5 hours. After cooling room temperature, 6.75 L of a 2N hydrochloric acid was dropped at 20–30° C. After phase separation, the water layer was extracted with 6.75 L of toluene. The organic layers were combined together and washed with 4.5 L of a 2N hydrochloric acid, two 5-L portions of a 2N aqueous sodium hydroxide solution, two 4.5-L portions of a 12.5% aqueous ammonia, 4.5 L of a 20% brine, 4.5 L of a 2N hydrochloric acid, and three 4.5-L portions of a 20% brine. After addition of 15 g or activated carbon (Shirasagi A), followed by stirring at room temperature for 20 minutes, filtration was conducted and the residue was washed with 1.3 L of toluene. Through vacuum concentration, 533.2 g of crude 2-fluoro-5-(4-propoxyethoxyphenyl) benzaldehyde was obtained as a brown oily matter, which was used in the next step without being purified. A part thereof was purified by column chromatography to yield 2-fluoro-5-(4-propoxyethoxyphenyl) benzaldehyde as white crystals.

$^1$H-NMR (CDCl$_3$, δ, 300 MHz); 0.94 (3H, t, J=7.44 Hz), 1.58–1.70 (2H, m), 3.51 (2H, t, J=6.78 Hz), 3.81 (2H, t, J=5.07 Hz), 4.16 (2H, t, J=4.71 Hz), 6.98 (2H, m), 7.01–7.25 (1H, m), 7.46–7.50 (2H, m), 7.74–7.77 (1H, m), 8.00–8.03 (1H, m), 10.40(1H, s)

Example 16

Production of ethyl 7-(4-propoxyethoxyphenyl)-2,3-dihydro-1-benzothiepine-4-carboxylate Under a nitrogen flow, 533.2 g of crude 2-fluoro-5-(4-propoxyethoxyphenyl)benzaldehyde was dissolved in 894 ml of N,N-dimethylformamide and cooled to 10° C. or lower 1,8-Diazabicyclo[5.4.0]-7-undecene (450 g, 2.956 mol) was added while keeping the mixture at 0–10° C. After dropping ethyl 4-mercaptobutyrate (438 g, 2.956 mol) slowly, the mixture was heated to 20° C. and then stirred at 20–30° C. for 1 hour. At 20–30° C., 8940 ml of diethyl carbonate was added and subsequently a solution of 20% sodium ethoxide (2012 g and 5.912 mol) in ethanol was dropped. The mixture was stirring at 20–30° C. for 3 hours and then cooled to 5° C. After adding 4.35 L of a 2N hydrochloric acid while maintaining the temperature at 10° C. or lower, phase separation was conducted and the water layer was extracted with 3.75 L of ethyl-acetate. The organic layers were combined and washed with 4 L of water, 4 L of a 5% aqueous sodium hydrogencarbonate solution, and 4 L of a 5% brine. Activated carbon Shirasagi A (45 g) and then tri-n-butyl phosphine (51 ml) were added. The mixture was stirred at room temperature for 20 minutes and then filtered. The residue was washed with 1.2 L of ethyl acetate. The filtrate was concentrated under vacuum, 1.2 L of isopropanol was added and then vacuum concentration was conducted (twice). After addition of 1.2 L of isopropyl ether and vacuum concentration, 900 ml of isopropyl ether was added to the oily matter obtained. Crystals formed during stirring at room temperature were dissolved by heating under reflux. After cooling and stirring for 2.5 hours and stirring for 2 hours while cooling in ice, the mixture was filtered and the residue was washed with 900 ml of ice-cooled isopropyl ether. Through vacuum drying (40° C.), 344.8 g (Yield from 5-bromo-2-fluorobenzaldehyde: 57%) of ethyl 7-(4-propoxyethoxyphenyl)-2,3-dihydro-1-benzothiepine-4-carboxylate was obtained as pale yellow crystals.

$^1$H-NMR (CDCl$_3$, δ, 300 MHz); 0.94 (3H, t, J=7.35 Hz), 1.36 (3H, t, J=7.19 Hz), 1.58,–1.71 (2H, m), 3.00 (2H, t, J=6.05 Hz), 3.22 (2H, t, J=5.81 Hz), 3.51 (2H, t, J=6.79 Hz), 3.81 (2H, J=4.95 Hz), 4.16 (2H, t, J=4.32 Hz), 4.29 (2H, q, J=7.11 Hz), 6.98–7.02 (2H, m), 7.36–7.57 (5H, m), 7.87(1H, s)

Referential Example 12

Production of ethyl 7-(4-propoxyethoxyphenyl)-1,1-dioxo-2,3-dihydro-1-benzothiepine-4-carboxlate Ethyl 7-(4-propoxyethoxyphenyl)-2,3-dihydro-1-benzothiepine-4-carboxylate (45 g, 109.1 mmol) was suspended in 405 ml of acetic acid and was heated to 60° C. to dissolve. A solution of 30% hydrogen peroxide (25.35 g, 223.6 mmol) in 45 ml of acetic acid was dropped slowly at 60–70° C. After the dropping, the mixture was stirred at 65–70° C. for 3 hours. At that temperature, 40 ml of an aqueous sodium sulfite solution was dropped and disappearance of the peroxide was checked with iodo-starch paper. After dropping 275 ml of water at that temperature, the mixture was cooled and stirred for 2 hours and then was stirred at 0–10° C. for 30 minutes. After filtration, the residue was washed with an ice-cooled, mixed solution of acetic acid/water (45 ml/31.5 ml) and subsequently with 225 ml of water. After vacuum drying (40° C.), 45.9 g (Yield 94.6%) of ethyl 7-(4-propoxyethoxyphenyl)-1,1-dioxo-2,3-dihydro-1-benzothiepine-4-carboxylate was obtained as white crystals.

$^1$H-NMR (CDCl$_3$, δ, 300 MHz); 0.94 (3H, t, J=7.38 Hz), 1.37 (3H, t, J=7.26 Hz), 1.60–1.71 (2H, m), 3.13 (2H, t, J=6.60 Hz), 3.51 (2H, t, J=6.75 Hz), 3.63 (2H, t, J=6.33 Hz), 3.82 (2H, J=5.04 Hz), 4.18 (2H, t, J=4.47 Hz), 4.31 (2H, q, J=7.23 Hz), 7.02–7.06 (2H, m), 7.53–7.57 (2H, m), 7.65–7.69 (2H, m), 7.89 (1H, s), 8.19(1H, d, J=8.01 Hz)

Referential Example 13

Production of 7-(4-propoxyethoxyphenyl)-1,1-dioxo-2,3-dihydro-1-benzothiepine-4-carboxlic acid Ethyl 7-(4-propoxyethoxyphenyl)-1,1-dioxo-2,3-dihydro-1-benzothiepine-4-carboxlate (11 g, 24.7447 mmol) was dissolved in 110 ml of tetrahydrofuran and 55 ml of methanol, and then 93.5 ml of water was added. After adding potassium carbonate (6.84 g, 49.49 mmol), the mixture was heated under reflux for 4.5 hours. Under reflux, 39.6 ml of a 3N hydrochloric acid and 40 ml of water were dropped. After cooling, the mixture was stirred for 1 hour while cooling in ice. After filtration, the residue was washed with 88 ml of water. After vacuum drying (40° C.), 9.4 g (Yield 91.2%) of 7-(4-propoxyethoxyphenyl)-1,1-dioxo-2,3-dihydro-1-benzothiepine-4-carboxylic acid was obtained as pale yellowish white crystals.

$^1$H-NMR (DMSO-d$_6$, δ, 300 MHz); 0.87 (3H, t, J=7.37 Hz), 1.49–1.57 (2H, m), 2.98 (2H, t, J=6.20 Hz), 3.42 (2H, t, J=6.65 Hz), 3.71–3.77 (4H, m), 4.14–4.18 (2H, m), 7.06–7.10 (2H, m), 7.76–7.79 (2H, m), 7.85–7.89 (2H, m), 8.04–8.07(2H, m)

Referential Example 14

Production of N-[4-[N-methyl-N-(tetrahydropyran-4-yl)aminomethyl]phenyl]-7-(4-propoxyethoxyphenyl)-1,1-dioxo-2,3-dihydro-1-benzothiepine-4-carboxamide 7-(4-Propoxyethoxyphenyl)-1,1-dioxo-2,3-dihydro-1-benzothiepine-4-carboxlic acid (20.0 g, 48.0202 mmol) was suspended in 100 ml of N,N-dimethylacetamide and thionyl chloride (3.68 ml, 50.42 mmol) was added at room temperature. After stirring at room temperature for 2 hours, an acid chloride solution was obtained as a homogeneous solution. 4-[N-methyl-N-(tetrahydropyran-4-yl) aminomethyl]aniline dihydrochloride (16.9 g, 57.6244 mmol) was suspended in 270 ml of N,N-dimethylacetamide and triethylamine (52.2 ml, 374.56 mmol) was added at room temperature, followed by being stirred at room temperature for 1 hour and 15 minutes. During cooling of the mixture in ice, the acid chloride solution previously obtained was dropped at 0–10° C. (washed up with 30 ml of N,N-dimethylacetamide). Stirring was done at room temperature for 2 hours and then 200 ml of water was dropped slowly. After stirring at room temperature for 1 hour, the crystals were filtered and washed with 100 ml of water and 100 ml of methanol. After vacuum drying, 24.6 g (Yield 83%) of N-[4-[N-methyl-N-(tetrahydropyran-4-yl)aminomethyl] phenyl]-7-(4-propoxyethoxyphenyl)-1,1-dioxo-2,3-dihydro-1-benzothiepine-4-carboxamide was obtained as yellowish white crystals.

$^1$H-NMR (CDCl$_3$, δ, 300 MHz); 0.94 (3H, t, J=7.42 Hz), 1.61–1.78 (6H, m), 2.20 (3H, s), 2.55–2.65 (1H, m), 3.13 (2H, t, J=6.61 Hz), 3.33–3.38 (2H, m), 3.49–3.55 (4H, m), 3.67 (2H, t, J=6.28 Hz), 3.82 (2H, t, J=4.94 Hz), 4.01–4.07 (2H, m), 4.18 (2H, t, J=4.63 Hz), 7.00–7.04 (2H, m), 7.27–7.34 (3H, m), 7.46–7.59 (6H, m), 8.11–8.18 (2H, m)

INDUSTRIAL APPLICABILITY

According to the present invention, it is possible to produce 2,3-dihydrothiepine derivatives in short processes, with safety, in methods suitable for large-scale synthesis.

What is claimed is:
1. A process for preparing a compound represented by the following formula:

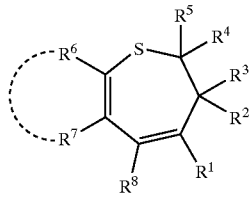

wherein each symbol is as defined below, or a salt thereof, characterized by subjecting a compound represented by the following formula:

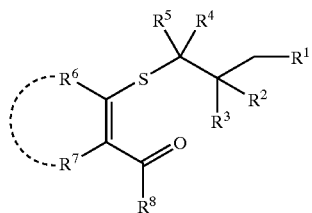

wherein $R^1$ is an electron-attracting group; $R^2$, $R^3$, $R^4$, $R^5$, $R^6$ and $R^7$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, provided that $R^6$ and $R^7$ may be united to form a ring; and $R^8$ is a hydrogen atom or an optionally substituted hydrocarbon group, or a salt thereof, to a ring-closing reaction.

2. The preparation process according to claim 1 wherein $R^1$ is an esterified carboxyl group.

3. The preparation process according to claim 1 wherein $R^8$ is a hydrogen atom.

4. The preparation process according to claim 1 wherein $R^2$, $R^3$, $R^4$ and $R^5$ are each a hydrogen atom.

5. The preparation process according to claim 1 wherein the reaction is conducted in the presence of a base.

6. The preparation process according to claim 5 wherein the base is an alcoholate.

7. The preparation process according to claim 1 wherein the reaction is conducted in a solvent containing a carbonic acid diester.

8. A process for preparing a compound represented by the following formula:

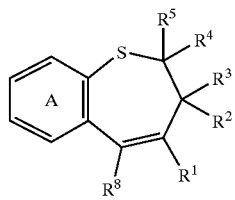

wherein each symbol is as defined below, or a salt thereof, characterized by subjecting a compound represented by the following formula:

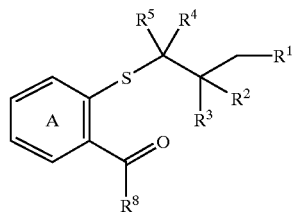

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; ring A is an optionally substituted benzene ring; and $R^8$ is a hydrogen atom or an optionally substituted hydrocarbon group, or a salt thereof, to a ring-closing reaction.

9. The preparation process according to claim 8 wherein $R^1$ is an esterified carboxyl group.

10. The preparation process according to claim 8 wherein $R^8$ is a hydrogen atom.

11. The preparation process according to claim 8 wherein $R^2$, $R^3$, $R^4$ and $R^5$ are each a hydrogen atom.

12. The preparation process according to claim 8 wherein the reaction is conducted in the presence of a base.

13. The preparation process according to claim 12 wherein the base is an alcoholate.

14. The preparation process according to claim 8 wherein the reaction is conducted in a solvent containing a carbonic acid diester.

15. A process for preparing a compound represented by the following formula:

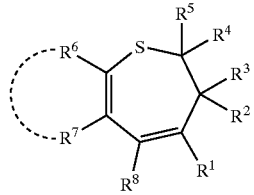

wherein each symbol is as defined below, or a salt thereof, characterized by causing a compound represented by the following formula:

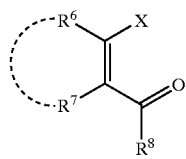

wherein X is a leaving group; and $R^6$ and $R^7$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, provided that $R^6$ and $R^7$ may be united to form a ring; and $R^8$ is a hydrogen atom or an optionally substituted hydrocarbon group, or a salt thereof, to react with a compound represented by the following formula:

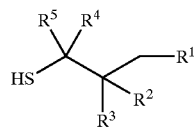

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, or a salt.

16. The preparation process according to claim 15 wherein X is a halogen atom.

17. The preparation process according to claim 15 wherein X is a fluorine atom.

18. The preparation process according to claim 15 wherein $R^1$ is an esterified carboxyl group.

19. The preparation process according to claim 15 wherein $R^8$ is a hydrogen atom.

20. The preparation process according to claim 15 wherein $R^2$, $R^3$, $R^4$ and $R^5$ are each a hydrogen atom.

21. A process for preparing a compound represented by the following formula:

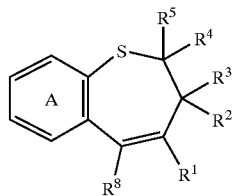

wherein each symbol is as defined below, or a salt thereof, characterized by causing a compound represented by the following formula:

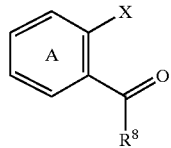

wherein X is a leaving group; $R^8$ is a hydrogen atom or an optionally substituted hydrocarbon group; and ring A is an optionally substituted benzene ring, or a salt thereof, to react with a compound represented by the following formula:

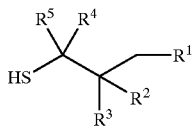

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group, or a salt thereof.

22. The preparation process according to claim 21 wherein X is a halogen atom.

23. The preparation process according to claim 21 wherein X is a fluorine atom.

24. The preparation process according to claim 21 wherein $R^1$ is an esterified carboxyl group.

25. The preparation process according to claim 21 wherein $R^8$ is a hydrogen atom.

26. The preparation process according to claim 21 wherein $R^2$, $R^3$, $R^4$ and $R^5$ are each a hydrogen atom.

27. A process for preparing a compound represented by the following formula:

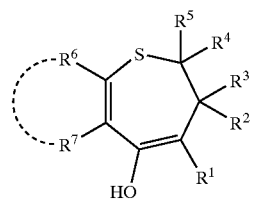

wherein each symbol is as defined below, or a salt thereof, characterized by subjecting a compound represented by the following formula:

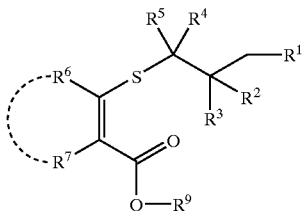

wherein $R^1$ is an electron-attracting group; $R^2$, $R^3$, $R^4$, $R^5$, $R^6$ and $R^7$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; and $R^9$ is an optionally substituted hydrocarbon group; provided that $R^6$ and $R^7$ may be united to form a ring, or a salt thereof, to a ring-closing reaction in the presence of an alcoholate in a solvent containing a carbonic acid diester.

28. The preparation process according to claim 27 wherein $R^1$ is an esterified carboxyl group.

29. The preparation process according to claim 27 wherein $R^2$, $R^3$, $R^4$ and $R^5$ are each hydrogen.

30. A process for preparing a compound represented by the following formula:

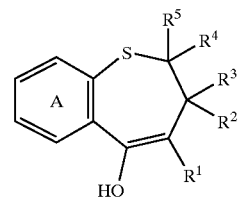

wherein each symbol is as defined below, or a salt thereof, characterized by subjecting a compound represented by the following formula:

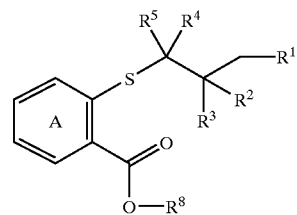

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; $R^9$ is an optionally substituted hydrocarbon group; and ring A is an optionally substituted benzene ring, or a salt thereof, to a ring-closing reaction in the presence of an alcoholate in a solvent containing a carbonic acid diester.

31. The preparation process according to claim 30 wherein $R^1$ is an esterified carboxyl group.

32. The preparation process according to claim 30 wherein $R^2$, $R^3$, $R^4$ and $R^5$ are each hydrogen.

33. A compound represented by the following general formula:

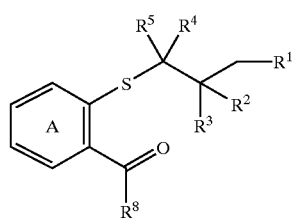

wherein $R^1$ is an electron-attracting group; $R^2$, $R^3$, $R^4$ and $R^5$ are each a hydrogen atom, a halogen atom, an optionally substituted amino group, an optionally substituted hydroxyl group, an optionally substituted thiol group, an optionally substituted hydrocarbon group, or an optionally substituted heterocyclic group; ring A is an optionally substituted benzene ring; and $R^8$ is a hydrogen atom or an optionally substituted hydrocarbon group, or a salt thereof.

34. The preparation process according to claim 33 wherein $R^1$ is an optionally esterified carboxyl group.

35. The preparation process according to claim 33 wherein $R^8$ is a hydrogen atom.

36. The preparation process according to claim 33 wherein $R^2$, $R^3$, $R^4$ and $R^5$ are each a hydrogen atom.

* * * * *